(12) United States Patent
Kim

(10) Patent No.: US 10,702,413 B2
(45) Date of Patent: Jul. 7, 2020

(54) LEG PROTECTOR AND SHOE SOLE FOR SAME

(71) Applicant: Choonghwan Kim, Seoul (KR)

(72) Inventor: Choonghwan Kim, Seoul (KR)

( * ) Notice: Subject to any disclaimer, the term of this patent is extended or adjusted under 35 U.S.C. 154(b) by 71 days.

(21) Appl. No.: 16/196,312

(22) Filed: Nov. 20, 2018

(65) Prior Publication Data

US 2019/0142622 A1   May 16, 2019

Related U.S. Application Data

(63) Continuation of application No. 16/085,438, filed as application No. PCT/KR2017/002757 on Mar. 14, 2017.

(30) Foreign Application Priority Data

| Mar. 15, 2016 | (KR) | 10-2016-0031131 |
| Mar. 16, 2016 | (KR) | 10-2016-0031577 |
| May 31, 2016 | (KR) | 10-2016-0066972 |

(51) Int. Cl.
| A43B 3/24 | (2006.01) |
| A61F 5/01 | (2006.01) |
| A41D 13/06 | (2006.01) |
| A43B 13/14 | (2006.01) |

(Continued)

(52) U.S. Cl.
CPC ........ *A61F 5/0195* (2013.01); *A41D 13/0543* (2013.01); *A41D 13/06* (2013.01); *A43B 3/24* (2013.01); *A43B 3/244* (2013.01); *A43B 3/246* (2013.01); *A43B 13/14* (2013.01); *A61F 5/0111* (2013.01); *A61F 5/0585* (2013.01)

(58) Field of Classification Search
CPC .......... A43B 3/24; A43B 3/244; A43B 23/08; A43B 23/081; A61F 5/0195; A61F 5/0111; A61F 5/0585
USPC ............................ 36/72 R, 77 R, 77 M, 110
See application file for complete search history.

(56) References Cited

U.S. PATENT DOCUMENTS

| 4,177,583 A | 12/1979 | Chapman |
| 4,542,599 A | 9/1985 | Annovi |

(Continued)

FOREIGN PATENT DOCUMENTS

| EP | 2147664 A1 | 1/2010 |
| KR | 101243558 B1 | 3/2013 |
| KR | 20150019768 A | 2/2015 |

OTHER PUBLICATIONS

International Search Report dated Jul. 10, 2017.

*Primary Examiner* — Marie D Bays
(74) *Attorney, Agent, or Firm* — Dinsmore & Shohl LLP; Yongsok Choi, Esq.

(57) ABSTRACT

The present disclosure relates to a leg protector. According to an aspect of the present disclosure, disclosed is a leg protector which can protect a wearer's foot and leg and is made of an elastic material, the leg protector comprising: a bottom plate part for supporting a wearer's foot; and a protection part connected to the upper side of the bottom plate part, extending upward therefrom, and formed to cover at least a part of the side and rear portions of the wearer's foot and leg, wherein the protection part includes, on both the left and right sides of the ankle portion thereof, an opening part through which regions corresponding to the wearer's malleoli are exposed to the outside.

4 Claims, 28 Drawing Sheets

(51) Int. Cl.
*A41D 13/05* (2006.01)
*A61F 5/058* (2006.01)

(56) References Cited

U.S. PATENT DOCUMENTS

| | | | |
|---|---|---|---|
| 4,811,501 A * | 3/1989 | Okayasu | A43C 13/14 36/77 R |
| 4,995,174 A * | 2/1991 | Hong | A43C 13/14 36/72 R |
| 5,926,978 A * | 7/1999 | Smith | A43B 3/24 36/101 |
| 6,283,932 B1 | 9/2001 | Munch et al. | |
| 2003/0145490 A1 * | 8/2003 | Tsai | A43B 3/122 36/15 |
| 2004/0187346 A1 * | 9/2004 | Bianchi | A43B 3/244 36/11.5 |
| 2006/0064902 A1 * | 3/2006 | Ashton | A43B 23/24 36/72 R |
| 2007/0068045 A1 * | 3/2007 | Condie | A43B 3/242 36/101 |
| 2007/0130802 A1 * | 6/2007 | Condie | A43B 3/24 36/101 |
| 2009/0229145 A1 * | 9/2009 | Ortner | A43B 3/24 36/100 |
| 2009/0287127 A1 | 11/2009 | Hu et al. | |
| 2010/0263237 A1 * | 10/2010 | Cuellar | A43B 3/105 36/136 |
| 2011/0258882 A1 | 10/2011 | Jones et al. | |
| 2012/0011742 A1 * | 1/2012 | Yang | A43B 23/081 36/45 |
| 2013/0219751 A1 | 8/2013 | Catlett | |
| 2014/0053433 A1 | 2/2014 | Delaney | |
| 2014/0128789 A1 | 5/2014 | Chen | |
| 2014/0196307 A1 * | 7/2014 | Fremming | A43B 1/0027 36/15 |
| 2014/0265018 A1 | 9/2014 | Grim et al. | |
| 2018/0325208 A1 * | 11/2018 | Delaney | A43B 23/0295 |
| 2019/0313730 A1 * | 10/2019 | Reuben | A43B 7/085 |

* cited by examiner

LEG PROTECTOR AND SHOE SOLE FOR SAME

CROSS REFERENCE TO RELATED APPLICATION(S)

This application is a continuation of U.S. patent application Ser. No. 16/085,438 filed on Sep. 14, 2018 which is a national stage of Patent Cooperation Treaty (PCT) International Application Serial No. PCT/KR2017/002757, filed on Mar. 14, 2017, which claims priority to Korean Patent Application No. 10-2016-0031131 filed on Mar. 15, 2016, Korean Patent Application No. 10-2016-0031577 filed on Mar. 16, 2016, and Korean Patent Application No. 10-2016-0066972 filed on May 31, 2016, the entire contents of which are hereby incorporated by reference.

FIELD OF THE INVENTION

The present disclosure relates to a leg protector and a shoe soles for the same, and more particularly, to a leg protector capable of providing a solid protective state by being pressed against and fixed to a foot and a leg in a state in which the foot or the leg is fractured or strained, being applied to both of left and right legs in a single shape, being easily detached, and allowing easy walking indoors and outdoors, and a shoe soles for the same.

BACKGROUND

When a foot or a leg has an injury such as a strain or a fracture, a stable protection is required to minimize a movement of the foot or the leg, as well as physical therapy. To this end, medical measures have been conventionally taken to help recover the injured portion by firmly fixing the foot or the leg firmly with a splint or a cast.

However, the splint or the cast has an advantage of being capable of firmly protect the injured leg, while there is a disadvantage in that various members are required to fix the foot or the leg and a movement of a wearer's leg or foot is excessively limited to cause a difficulty in simple walking.

In consideration of the foregoing, it has been commercially proposed a shoe-shaped protector for partially fixing a foot, or a cast-shaped leg protector made of a synthetic resin material.

However, since conventional commercial products still focus on fixing an injured portion, there are limitations in simultaneously providing various functions such as allowing a movement such as simple walking, detachable convenience, and movement convenience indoors and outdoors.

SUMMARY OF THE INVENTION

The present disclosure is directed to providing a leg protector capable of providing a solid protective state by being pressed against and fixed to a foot and a leg in a state in which the foot or the leg is fractured or strained, being applied to both of left and right legs in a single shape, being easily detached, and allowing easy walking indoors and outdoors, and a shoe soles for the same.

One aspect of the present disclosure provides a leg protector made of an elastic material to protect a foot and a leg, the leg protector including a bottom plate part configured to support the foot, and a protection part formed to be connected to an upper side of the bottom plate part and to surround at least a portion of a lateral surface portion and a rear surface portion of each of the foot and the leg, wherein the protection part includes an opening part provided at both of left and right sides around an ankle and configured to expose a portion corresponding to a position of a malleolus of a wearer to the outside.

The bottom plate part may include a front bottom plate part located at a front side of the foot and configured to not be connected to the protection part surrounding the lateral surface portion of the foot, and a rear bottom plate part located at a rear side of the foot and configured to be integrally connected to the protection part surrounding the lateral surface portion of the foot, wherein elastic bending deformation of the bottom plate part is generated due to a walking weight of the wearer, and elastic bending deformation of the front bottom plate part is generated to be greater than elastic bending deformation of the rear bottom plate part.

The leg protector may further include a toe cover part provided at an upper portion of a front surface portion of the bottom plate part and formed to surround toes from an upward side of the toes, and a detachable coupling part formed at a position of one side of the toe cover part and configured to allow the toe cover part to be detachable even in a state in which the leg protector is worn.

The leg protector may further include a first sole including a first sole plate part provided at a lower portion of the bottom plate part and having a first curved part in which a plurality of curves are disposed in a front-rear direction of the foot at a lower surface of the first sole plate part, and a plurality of lateral protrusions formed along a lateral surface of the first sole plate part, and a second sole including a second sole plate part detachably coupled to a lower portion of the first sole and having a second sole plate part with a second curved part formed in a curved shape corresponding to a shape of the first curved part at an upper surface of the second sole plate part and a lateral wall formed along an edge of the second sole plate part and having a protrusion insertion recess, at an inner surface of the lateral wall, configured to allow each of the plurality of lateral protrusions to be insertable into the protrusion insertion recess.

The bottom plate part and the protection part may be integrally formed to be connected using the same elastic synthetic material and may respectively include a plate-shaped part configured to support a body of the wearer and a connector configured to connect the plate-shaped part to the bottom plate part and the protection part, and a thickness of the connector may be formed to be thinner than that of the plate-shaped part.

Another aspect of the present disclosure provides a shoe sole including a first sole including a first sole plate part provided at a lower portion of a bottom plate part of a show and having a first curved part in which a plurality of curves are disposed in a front-rear direction of the foot at a lower surface of the first sole plate part, and a plurality of lateral protrusions formed along a lateral surface of the first sole plate part, and a second sole including a second sole plate part detachably coupled to a lower portion of the first sole and having a second sole plate part with a second curved part formed in a curved shape corresponding to a shape of the first curved part at an upper surface of the second sole plate part and a lateral wall formed along an edge of the second sole plate part and having a protrusion insertion recess, at an inner surface of the lateral wall, configured to allow each of the plurality of lateral protrusions to be insertable into the protrusion insertion recess.

In accordance with the present disclosure, when a fracture, a sprain, a bruise, or the like occurs at a foot or a leg and thus the foot or the leg should be protected, there is an advantage in that the foot and the leg are entirely fixed and protected without a cast to allow patients to recover quickly from injury.

Particularly, the present disclosure has an advantage capable of being applied without distinction of left and right legs, having a slimmed shape, being pressed and fixed to the foot and the leg, thereby providing an excellent feeling of wearing.

Further, in accordance with the present disclosure, there is an advantage in that a leg protector can be easily detached and appropriately applied to different thicknesses, different shapes, and the like of wearers, thereby firmly fixing the leg.

Furthermore, in accordance with the present disclosure, even in a state in which the leg protector is worn, there is an advantage in that a cover for protecting toes can be easily detached to provide convenience of leg protector detachment and ventilation.

Moreover, in accordance with the present disclosure, since a structure of firmly fixing the leg and an ankle and partially allowing a movement of a sole mainly on a front portion of the sole is provided, there is an advantage capable of protecting an injured portion and allowing a patient to perform a daily walking when light injury such as a strain occurs at the leg or the ankle.

Additionally, in accordance with the present disclosure, in a state in which the foot and the leg are protected, there is an advantage in that various activities including a walking indoors and outdoors can be freely and comfortably performed through a sole detachment structure.

Particularly, in accordance with the present disclosure, a patient can move from indoors to outdoors and vice versa by detaching only a second sole such that there is an advantage in that the patient does not detach the leg protector or replace the leg protector with another shoe for movement.

DETAILED DESCRIPTION OF THE PREFERRED EMBODIMENTS

The present disclosure may be practiced in various other forms without departing from the spirit or essential features of the present disclosure. Accordingly, exemplary embodiments of the present disclosure should not be construed as only illustrative and restrictive in all aspects.

The terms a first, a second, and the like are used only for the purpose of distinguishing one component from another component. For example, without departing from the scope of the present disclosure, a first component may be referred to as a second component, and similarly, a second component may also be referred to as a first component.

When a component is referred to as being "connected" or "coupled" to another component, it may be directly connected or coupled to another component, and yet another component may exist between the component and another component.

The singular forms used herein include plural forms unless the context clearly notes otherwise. In this disclosure, the terms "comprising," "including," "having," and the like are intended to describe the presence of components described herein or a combination thereof and are not intended to exclude probability of the presence or addition of other components or features in advance.

Also, in the following description of the present disclosure, when a detailed description of a known related art is determined to obscure the gist of the present disclosure, the detailed description thereof will be omitted.

A configuration of a leg protector according to the present embodiment will be described with reference to the drawings.

Figure 1:
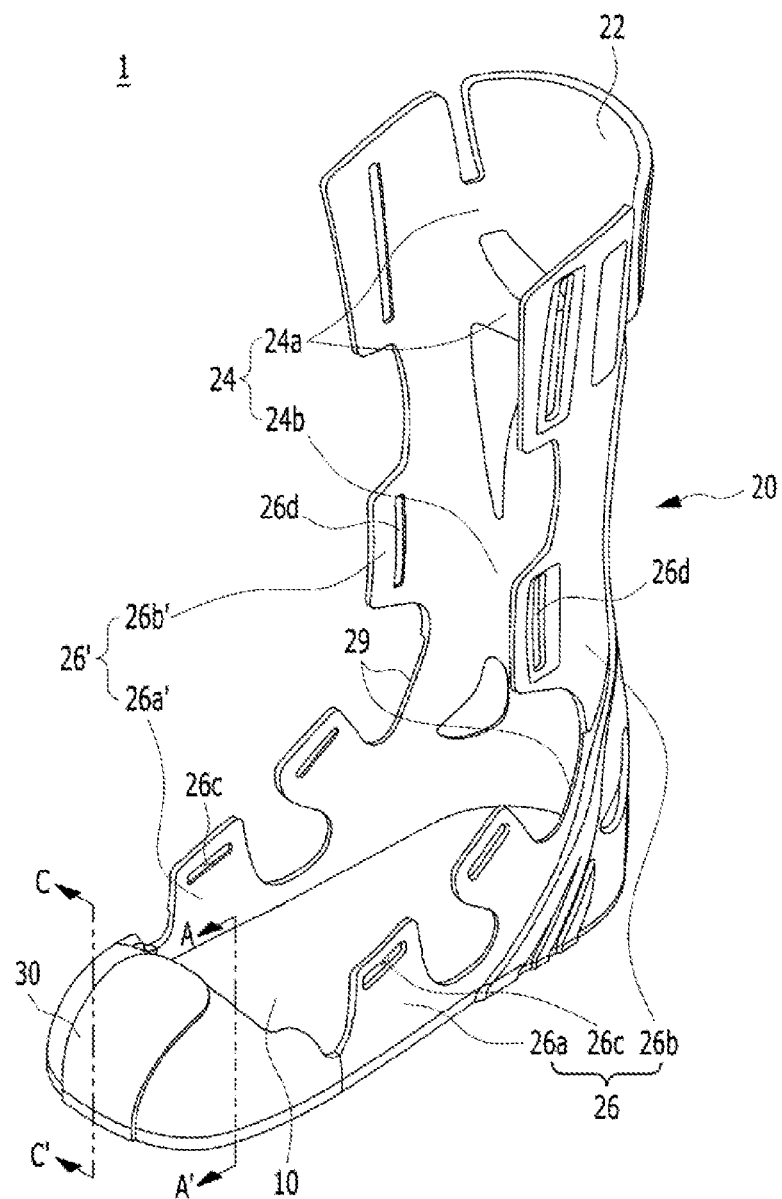
FIG. 1 is a perspective view of a leg protector according to one embodiment of the present disclosure.
Figure 2:
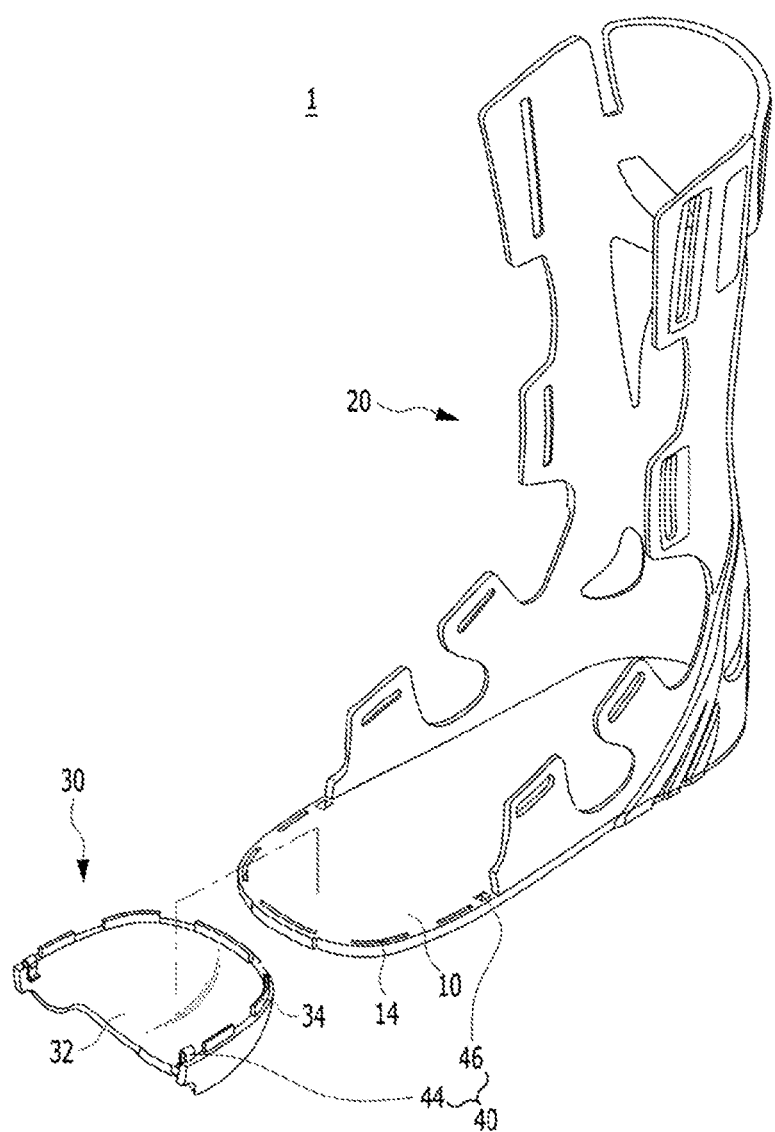
FIG. 2 is an exploded perspective view of the leg protector according to one embodiment of the present disclosure.

FIG. 1 is a perspective view of a leg protector according to one embodiment of the present disclosure. FIG. 2 is an exploded perspective view of the leg protector according to one embodiment of the present disclosure.

A leg protector 1 according to one embodiment of the present disclosure simultaneously protects a foot and a leg. The leg protector 1 is preferably made of an elastic material (e.g., a synthetic resin material, or a hard rubber material) so as to appropriately press, fix, and protect a foot and a leg by corresponding to sizes and shapes of the foot and the leg. As the synthetic resin material, polypropylene (PP), acrylonitrile-butadiene-styrene (ABS), polyethylene (PE), polycarbonate (PC), or a nylon resin may be used, and preferably, the nylon resin may be used. In order to control or enhance strength and elasticity properties, it is also possible to use a material mixed with a glass fiber or a carbon fiber as reinforcement. For example, the leg protector may be formed by injection molding using such a synthetic resin.

The leg protector 1 according to one embodiment of the present disclosure includes a bottom plate part 10 for supporting a foot, and a protection part 20 for fixing and protecting the foot and a leg.

For example, the bottom plate part 10 may be formed to have a planar shape of a left or right sole. Alternatively, the bottom plate part 10 may be formed to have a plate shape in which left and right sides are symmetrical and a front surface portion is wider than a rear surface portion so as to be applicable to both of left and right feet.

In terms used herein, a "left" and a "right" respectively mean left and right sides of the leg protector 1 in a state in which the leg protector 1 is worn, and in the same state, a "front surface" or a "front side" corresponds to a side that is closer to a toe and a "rear surface" or a "rear side" corresponds to a side that is closer to a heel.

As described above, in order to allow comfortable walking, the bottom plate part 10 is preferably made of a material having elasticity. A heel part (not shown) may be formed on a bottom surface of the bottom plate part 10 to prevent the bottom plate part 10 from being worn and to perform an appropriate angle adjustment of the heel.

The protection part 20 is formed to be connected to an upper side of the bottom plate part 10. Preferably, the protection part 20 is symmetrically formed to surround at least a portion of lateral surface portions and rear surface portions of the foot and the leg.

Preferably, the bottom plate part 10 and the protection part 20 may be integrally formed and connected to each other with a single elastic material and may appropriately provide a solid support function and a flexible deformation function with a thickness of the single elastic material and a coupling structure according to each of portions of the bottom plate part 10 and the protection part 20.

According to another aspect, the bottom plate part 10 and the protection part 20 may be preferably configured to be integrally formed (e.g., integrally press formed using a molten elastic material as a mold) so as to reduce costs through simplification of manufacturing and assembly processes.

Alternatively, the bottom plate part 10 and the protection part 20 may be formed to be coupled to each other via a coupling part (e.g., a coupling part, a rivet, a bolt, a nut, or the like mechanically formed at each of the bottom plate part 10 and the protection part 20).

The protection part 20 is formed to include an opening part 29 provided at both of left and right sides of an ankle region so as to expose portions corresponding to positions of malleolus of a wearer to the outside.

The opening part 29 are preferably and symmetrically provided between left and right leg protection plates 26b and 26b' and left and right foot protection plates 26a and 26a', and when the left and right leg protection plates 26b and 26b' are separated and the left and right foot protection plates 26a and 26a' are separated, the opening part 29 are preferably positioned at separated portions.

The opening part 29 prevents the malleolus of the wearer from being pressed when the wearer wears the leg protector 1 according to one embodiment of the present disclosure.

Further, since the opening part 29 are formed at both of the left and right sides, the protection parts 20 around the malleolus of the wearer wearing the leg protector 1 according to one embodiment of the present disclosure do not outwardly protrude such that the leg protector 1 may be formed to be slimmed in left and right widths.

Figure 4:
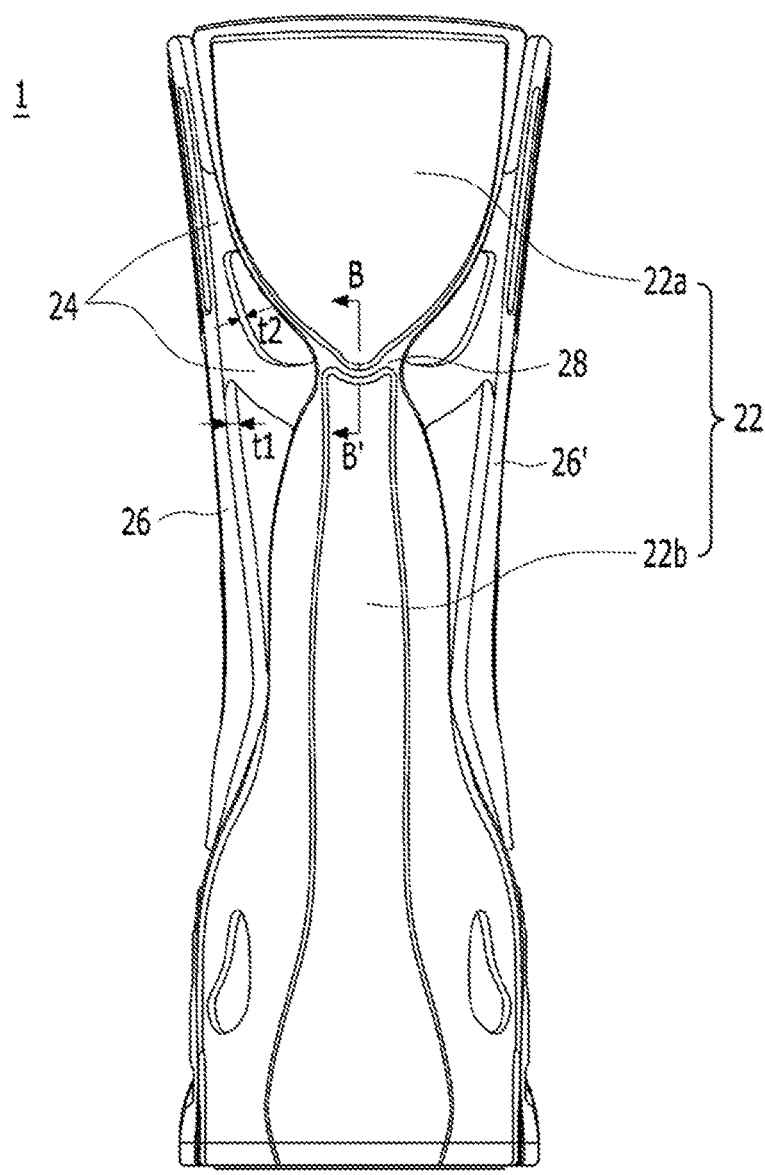
FIG. 4 is a rear view of the leg protector according to one embodiment of the present disclosure.
Figure 5:
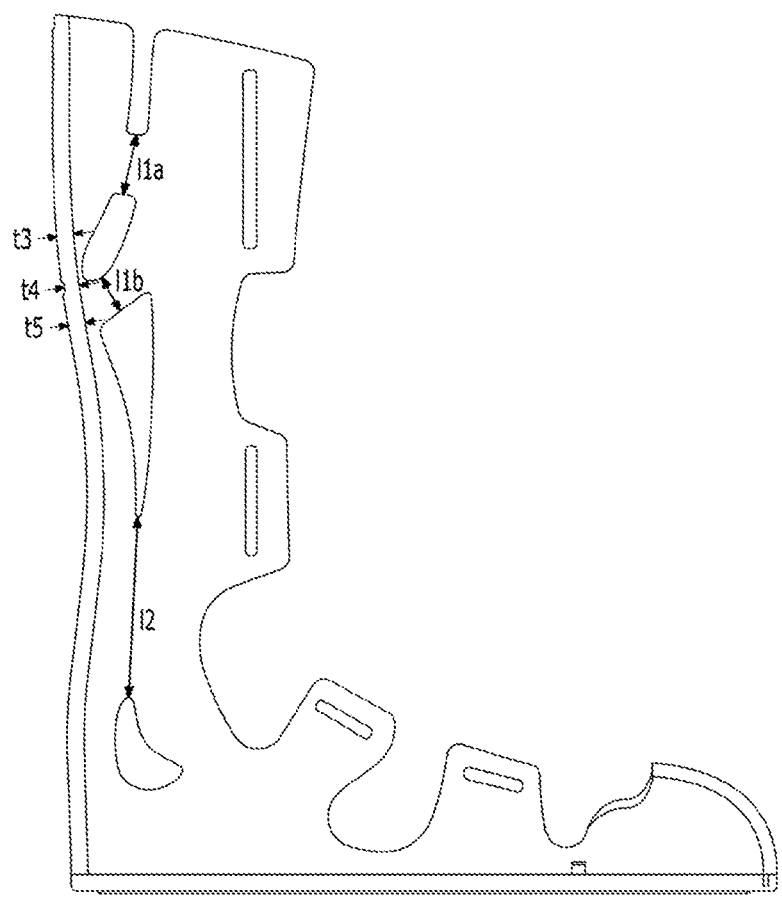
FIG. 5 is a side cross-sectional view of the leg protector according to one embodiment of the present disclosure.
Figure 6:
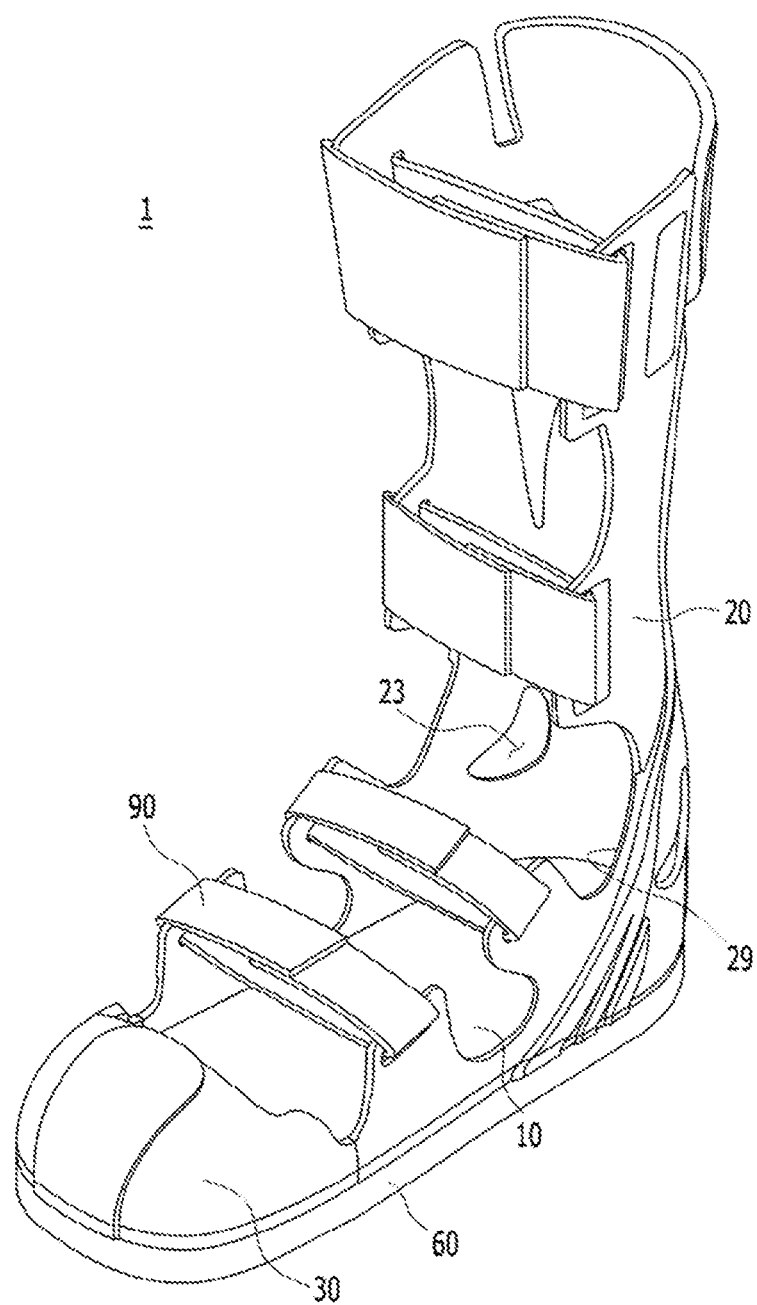
FIG. 6 is a perspective view of the leg protector with which a fastener is engaged according to one embodiment of the present disclosure.

FIG. 4 is a rear view of the leg protector according to one embodiment of the present disclosure, FIG. 5 is a side cross-sectional view of the leg protector according to one embodiment of the present disclosure and a cross-sectional view taken along the line B-B' of FIG. 4, and FIG. 6 is a perspective view of the leg protector with which a fastener is engaged according to one embodiment of the present disclosure.

As shown in FIG. 4, the protection part 20 according to one embodiment of the present disclosure includes a rear plate 22 for protecting a rear surface portion of a leg, and left and right lateral plates 26 and 26' for protecting lateral surface portions of a foot and the leg.

The rear plate 22 located at a rear surface portion of the protection part 20 supports a rear portion of the leg, and the left and right lateral plates 26 and 26' located at both lateral surfaces of the protection part 20 fix and protect the foot including a dorsum pedis while supporting both of lateral surfaces of the leg.

As shown in FIG. 4, the rear plate 22 and the left or right lateral plate 26 or 26' according to one embodiment of the present disclosure are formed to be connected by a first connector 24.

Preferably, the first connector 24 may be integrally formed with the rear plate 22 and the left or right lateral plate 26 or 26' and may be formed of an elastic material which is the same or similar to materials of the rear plate 22 and the left and right lateral plates 26 and 26'. Alternatively, the rear plate 22 and the left and right lateral plates 26 and 26' may be respectively formed of a relatively hard material, and the first connector 24 may be formed of a relatively soft material.

As a preferred embodiment, the first connector 24 of the present embodiment is made of a material, which is the same as materials of the rear plate 22 and the left and right lateral plates 26 and 26', and is formed to be thinner than a connection portion between the rear plate 22 and the left or right lateral plate 26 or 26'.

For example, as shown in FIG. 4, even when the rear plate 22 and the left and right lateral plates 26 and 26' are formed of the same elastic material, a thickness t2 of the first connector 24 is formed to be thinner that a thickness t2 of the connection portion of the left or right lateral plates 26 or 26' and a thickness (not shown) of the connecting portion of the rear plate 22 such that it may obtain an effect due to a relative thickness difference among the rear plate 22, the left or right lateral plate 26 or 26', the first connector 24, which is similar to an effect when the rear plate 22 and the left and right lateral plates 26 and 26' are respectively formed of a relatively hard material, and the first connector 24 is a relatively soft material.

Consequently, the rear plate 22 and the left and right lateral plates 26 and 26' have relatively hard characteristics such that the rear plate 22 and the left and right lateral plates 26 and 26' may have flexibility therebetween while firmly fixing a rear surface and lateral surfaces of the leg to stably surround the leg in all directions.

In other word, owing to a shape of the protection part 20, the rear plate 22 and the left and right lateral plates 26 and 26', each of which is made of a relatively hard material, are connected by the first connector 24 which is made of a relatively soft material such that it is possible to simultaneously obtain rigidity provided from a conventional splint and flexibility provided from a bandage (string) connecting the leg and the splint to press the leg.

The thickness of each of the connection portions may be understood as a thickness of a portion at which the rear plate 22, the left or right lateral plate 26 or 26', and the first connector 24 are directly connected.

The left or right lateral plate 26 or 26' according to one embodiment of the present disclosure includes a foot protection plate located at a front side and a leg protection plate positioned at a rear side.

For example, the foot protection plate is located at a lower front side of the opening, and the leg protection plate is located at an upper rear side of the opening. Positions of the foot protection plate and the leg protection plate mean approximate positions, and a portion of each of the foot protection plate and the leg protection plate may be formed to partially extend to a lower rear side or an upper front side about the opening.

The left lateral plate 26 includes the left foot protection plate 26a and the left leg protection plate 26b, and the right lateral plate 26' includes the right foot protection plate 26a' and the right leg protection plate 26b'.

The left and right foot protection plates 26a and 26a' protect a foot from external impact and damage while fixing the foot, and the left and right leg protection plates 26b and 26b' protect a leg from external impact and damage while fixing the leg.

The left and right foot protection plates 26a and 26a' and the left and right leg protection plates 26b and 26b' may be formed to be separated and to be connected by a connection member (not shown) having a shape similar to that of the above-described first connector 24 or a second connector 28, which will be described below, to surround better the foot and the leg while integrally fixing the foot and the leg.

For example, fastener engagement parts 26c and 26d are respectively formed at the left and right lateral plates 26 and 26', i.e., the left and right foot protection plates 26a and 26a' and the left and right leg protection plates 26b and 26b'.

As shown in FIG. 6, a fastener engagement part 26c may be formed at the foot protection plate to fix the foot at a side of the dorsum pedis, and a fastener engagement part 26d may be formed at the leg protection plate at a side of a front surface of the leg.

In this case, one or more fastener engagement parts 26c may be formed at each of the left and right foot protection plates 26a and 26a', and one or more fastener engagement parts 26d may be formed at each of the left and right leg protection plates 26b and 26b'.

A fastener 90 may be inserted into each of the fastener engagement parts 26c and 26d to fix and protect the foot and the leg, and in addition to a velcro type fastener 90 as shown in FIG. 6, various type known connection parts may be used.

The fastener 90 and the fastener engagement parts 26c and 26d facilitate detachment of the leg protector 1 according to one embodiment of the present disclosure.

At least a portion of a height range of the fastener engagement part 26d formed at each of the left and right leg protection plates 26b and 26b' according to one embodiment of the present disclosure overlaps with a height range of the first connector 24.

Such a height overlapping can be understood that at least a portion of a width of a fastener, which is engaged with the fastener engagement part 26d formed at each of the left and right leg protection plates 26b and 26b', and at least a portion of a width of the first connector 24 form a ring shape and are coplanar with each other.

Since a portion of the width of the fastener and a portion of the width of the first connector 24 are formed to constitute a single strip shape, even though the fastener is engaged with only the front surface as shown in FIG. 6, an effect of entirely fixing the leg by the fastener may be obtained such that the leg of the wearer may be tightly fixed.

As shown in FIG. 1, the first connector 24 according to one embodiment of the present disclosure includes a first upper connector 24a for connecting the rear plate 22 and upper ends of the left and right leg protection plates 26b and 26b' and a first lower connector 24b for connecting lower ends of the left and right leg protection plates 26b and 26b'.

One or more first upper connectors 24a and one or more first lower connectors 24b are formed, and as described above, one or more first upper connectors 24a and one or more first lower connectors 24b are preferably formed of materials which are the same as those of the rear plate 22 and the left and right leg protection plates 26b and 26b'.

For example, as shown in FIG. 1, two first upper connectors 24a are formed, and such a configuration allows the rear plate 22 and the left and right leg protection plates 26b and 26b' to fix more tightly the entire leg of the wearer.

In this case, a minimum value of a vertical width of the first upper connector 24a is formed to be equal to or less than a minimum value of a vertical width of the first lower connector 24b.

For example, as shown in FIG. 5, when two first upper connectors 24a are formed, a value ($11a+11b$) obtained by adding minimum values of both vertical widths of the two first upper connectors 24a are equal to or less than a minimum value 12 of the vertical width of the first lower connector 24b.

Since a lower portion of the leg adjacent to the foot should be fixed more firmly so as to not move when an ankle is fractured, the first lower connector 24b is preferably formed more firmly than the first upper connector 24a. Consequently, since high strength may be secured as a cross-sectional connection area becomes wider when the material and the thickness are same, so that the minimum value of the vertical width of the first upper connector 24a is preferably formed to be equal to or less than the minimum value of the vertical width of the first lower connector 24b.

As shown in FIG. 4, the rear plate 22 according to one embodiment of the present disclosure includes an upper plate 22a formed at an upper portion of the rear plate 22 and a lower plate 22b formed at a lower portion of the rear plate 22.

Generally, a leg of a person becomes thicker toward an upward side and becomes relatively thinner toward a downward side so that in order to stably fix a leg of a wearer wearing the leg protector 1 according to one embodiment of the present disclosure, it is preferable that upper and lower portions of the leg protector 1 are separately fixed.

Consequently, the upper plate 22a and the lower plate 22b may be formed to mutually move within a predetermined range. For example, the upper plate 22a and the lower plate 22b may be formed to be separated from each other. Alternatively, the upper plate 22a and the lower plate 22b may be formed to be connected by a separate connection part.

The upper plate 22a and the lower plate 22b according to one embodiment of the present disclosure are formed to be connected by the second connector 28.

Preferably, the second connector 28 may be integrally formed with the upper plate 22a and the lower plate 22b and may be made of an elastic material which is the same as or similar to materials of the upper plate 22a and the lower plate 22b. Alternatively, the upper plate 22a and the lower plate 22b may be made of relatively hard materials and the second connector 28 may be made of a relatively soft material.

As a preferred embodiment, the second connector 28 of the present embodiment is made of a material, which is the same as materials of the upper plate 22a and the lower plate 22b, and is formed to be thinner than a connection portion between the second connector 28 and the upper or lower plate 22a or 22b.

For example, as shown in FIG. 5, even when the upper plate 22a and the lower plate 22b are formed of the same elastic material, a thickness t4 of the second connector 28 is formed to be thinner that a thickness t3 of the connection portion of the upper plate 22a and a thickness t5 of the connection portion of the lower plate 22b such that it may obtain an effect due to a relative thickness difference among the second connector 28, the upper plate 22a, the lower plate 22b, which is similar to an effect when the upper plate 22a and the lower plate 22b are respectively formed of a relatively hard material, and the second connector 28 is a relatively soft material.

Consequently, the upper plate 22a and the lower plate 22b have relatively hard characteristics such that the upper plate 22a and the lower plate 22b may have flexibility therebetween while firmly fixing the upward side and the downward side of the leg to stably surround the leg in all directions.

The thickness of each of the connection portions can be understood as a thickness of a portion at which the upper plate 22a or the lower plate 22b is directly connected to the second connector 28.

The left and right lateral plates 26 and 26' according to one embodiment of the present disclosure are made of the same material and are respectively formed to have a thickness that is thinner than thicknesses of the upper plate 22a and the lower plate 22b.

That is, the upper plate 22a and the lower plate 22b supporting rear portions of the foot and the leg may be thickly formed to firmly support the rear portion of the leg, and the left and right lateral plates 26 and 26' may be formed to be relatively thinner such that both of lateral surfaces of the foot and the leg are tightly surrounded.

Consequently, the leg protector 1 according to one embodiment of the present disclosure is formed such that the left and right lateral plates 26 and 26' are formed to be thinner than the lower plate 22b and the upper plate 22a, and the first connector 24 and the second connector 28 are formed to be thinner than the left and right lateral plates 26 and 26'.

Preferably, a thickness of each of the lower plate 22b and the upper plate 22a is formed with 5 mm±0.5 mm so as to maintain rigidity and an appropriate weight, a thickness of each of the left and right lateral plates 26 and 26' is formed with 4 mm±0.4 mm, and a thicknesses of each of the first connector 24 and the second connector 28 is formed with 3 mm±0.3 mm.

One or more air holes 23 may be provided at the protection part 20 to reduce a weight of the leg protector 1 according to one embodiment of the present disclosure and facilitate sweat discharge and ventilation.

As shown in FIG. 6, the leg protector 1 according to one embodiment of the present disclosure may further include a shoe sole 60 provided at the bottom surface of the bottom plate part 10.

The shoe sole 60 may provide a cushioning feeling to the wearer to allow the wearer to comfortably walk in a state of wearing the leg protector 1 and may prevent abrasion of the leg protector 1.

For example, the shoe sole 60 may be formed to be detachable using a known press-fit type engagement structure. Alternatively, the shoe sole 60 may be fixedly formed by a method such as adhesion to the leg protector 1.

When the shoe sole 60 is formed to be detachable, the shoe sole 60 is detached from the leg protector 1 indoors and is attached to the leg protector 1 outdoors such that the wearer may move anywhere indoors and outdoors in a state of wearing the leg protector 1.

The leg protector 1 according to one embodiment of the present disclosure further includes a toe cover part 30 for protecting toes.

The toe cover part 30 is provided at an upward side of the front surface portion of the bottom plate part 10 and is formed to surround the toes from an upper side of the toes.

The toe cover part 30 can be understood as a part which corresponds to a shoe nose of a shoe and is capable of protecting the toes from external impact.

The toe cover part 30 may include a cover 32 for protecting the toes.

For example, as shown in FIG. 1, the cover 32 may be formed in a shape similar to a shape which is obtained by halving a hemisphere.

As shown in FIG. 2, the cover 32 may be configured such that an end portion of the cover 32 is coupled to an edge of the bottom plate part 10. In the present embodiment, the end portion of the cover 32 can be understood as a lower end edge of the cover 32 which is coupled to an upper surface of the bottom plate part 10.

Figure 3:
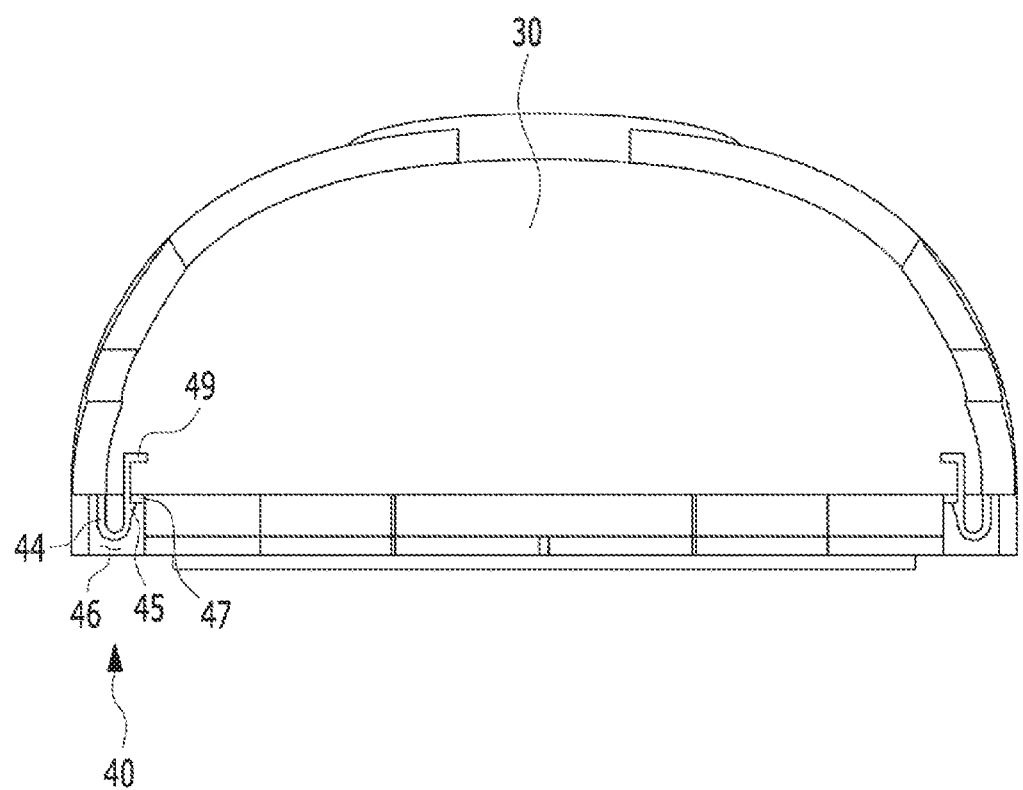
FIG. 3 is a cross-sectional view of the leg protector according to one embodiment of the present disclosure.

FIG. 3 is a cross-sectional view of the leg protector according to one embodiment of the present disclosure and is a cross-sectional view taken along the line A-A' of FIG. 1.

As shown in FIGS. 2 and 3, the leg protector 1 according to one embodiment of the present disclosure is formed at one side of a position of the toe cover part 30 and further includes a detachable coupling part 40 for allowing the toe cover part 30 to be detachable even in a state in which the leg protector 1 is worn.

For example, the detachable coupling part 40 is configured to be fitted and coupled by an elastic force.

The detachable coupling part 40 according to one embodiment of the present disclosure includes at least one elastic insertion piece 44 formed at an end portion of the cover 32 and an insertion hole 46 formed at a position of the bottom plate part 10 corresponding to the elastic insertion piece 44.

For example, a single elastic insertion piece 44 may be formed at each of left and right end portions of the cover 32.

For example, as shown in FIG. 3, the elastic insertion piece 44 includes a detachable part 49 formed in a U-shape and having one end connected to the end portion of the cover 32 and the other end exposed to an upper side of the insertion hole 46 in a state of being coupled.

The detachable part 49 is formed to be exposed to the upper side of the insertion hole 46 of the bottom plate part 10 in a state of being coupled such that the wearer may operate the detachable part 49 at the upper side of the bottom plate part 10. Preferably, a cushion pad (not shown) having a thickness in the range of about 3 mm to 7 mm may be bonded to the upper surface of the bottom plate part 10, and an uppermost end portion of the detachable part 49 may be formed to be slightly lower than an upper end surface of the cushion pad (not shown). In this case, in a state of being worn, since the uppermost end portion of the detachable part 49 is not exposed to be higher than the upper end surface of the cushion pad (not shown), the wearer does not experience inconvenience of a feeling of wearing and, when a detachment manipulation is required, the wearer is able to manipulate the uppermost end portion of the detachable part 49 in a state of slightly pressing the cushion pad to compress the cushion pad.

A size (width) of the U-shaped elastic insertion piece 44 before being contracted is formed to be larger than that of the insertion hole 46 so that, when the elastic insertion piece 44 is inserted into the insertion hole 46, the other end of the elastic insertion piece 44 (a side of the detachable part 49) may be pressed to be in contact with one lateral surface of the insertion hole 46.

At this time, since the elastic insertion piece 44 is not separated from the insertion hole 46 by a frictional force caused by the press contact, the toe cover part 30 and the bottom plate part 10 may be coupled and fixed to each other.

A hook part 45 may be further provided at one side of the other end of the elastic insertion piece 44. The hook part 45 is hooked to a hook bump 47 provided at one lateral surface of the insertion hole 46 at which the contact is made, thereby preventing easy detachment of the detachable coupling part 40 from the insertion hole 46.

Separation of the toe cover part 30 from the bottom plate part 10 may be achieved by inserting a finger into the toe cover part 30 to press outward the detachable part 49 in a state in which the leg protector 1 is worn.

To this end, the elastic insertion piece 44, particularly the detachable part 49, is preferably formed at a distal end portion of the cover.

Since the detachable coupling part 40 according to one embodiment of the present disclosure is formed at each of both sides of the end portion of the cover 32, even though the foot of the wearer is biased to one side to push the detachable part 49, coupling of the toe cover part 30 and the bottom plate part 10 may be maintained.

According to another embodiment of the present disclosure, one or more protruding insertion pieces 34 are formed at one side of the end portion of the cover 32, and a recess 14 into which the protruding insertion piece 34 is insertable is formed at a position of the bottom plate part 10 corresponding to each of the one or more protruding insertion pieces 34.

The protruding insertion piece 34 and the recess 14 are formed to firmly couple the toe cover part 30 and the bottom plate part 10 together with the detachable coupling part 40.

For example, in order to allow the protruding insertion piece 34 to be fixed to the recess 14 by a press-fit coupling, an interior size (a length and/or a width) of the recess 14 may be formed equal to or less than an exterior size (a length and/or a width) of the protruding insertion piece 34.

The protruding insertion piece 34 and the recess 14 are preferably formed around a front surface of the end portion of the cover 32 to prevent occurrence of a gap between the front surfaces of the toe cover part 30 and the bottom plate part 10.

A portion at which the cover 32 and the bottom plate part 10 according to one embodiment of the present disclosure are coupled (the protruding insertion piece 34 and the recess 14 are coupled and the detachable coupling parts 40 are coupled) is preferably configured to not be pressed by a sole of the wearer.

In this case, even though the bottom plate part 10 is pressed downward by a weight of the wearer wearing the leg protector 1 according to one embodiment of the present disclosure, a force is not applied to the cover 32 and thus detachment between the toe cover part 30 and the bottom plate part 10 is not affected such that the toe cover part 30 may be easily detached toward the upward side.

Meanwhile, the leg protector of the present embodiment is configured such that a protection part for surrounding lateral surfaces and rear surfaces of a foot and a leg and a bottom plate part for supporting the foot are integrally formed to be connected, a walking assist function of the wearer is provided through elastic bending deformation of the bottom plate part, and an injured area around an ankle is effectively protected. A detailed configuration thereof will be described below.

Figure 7:
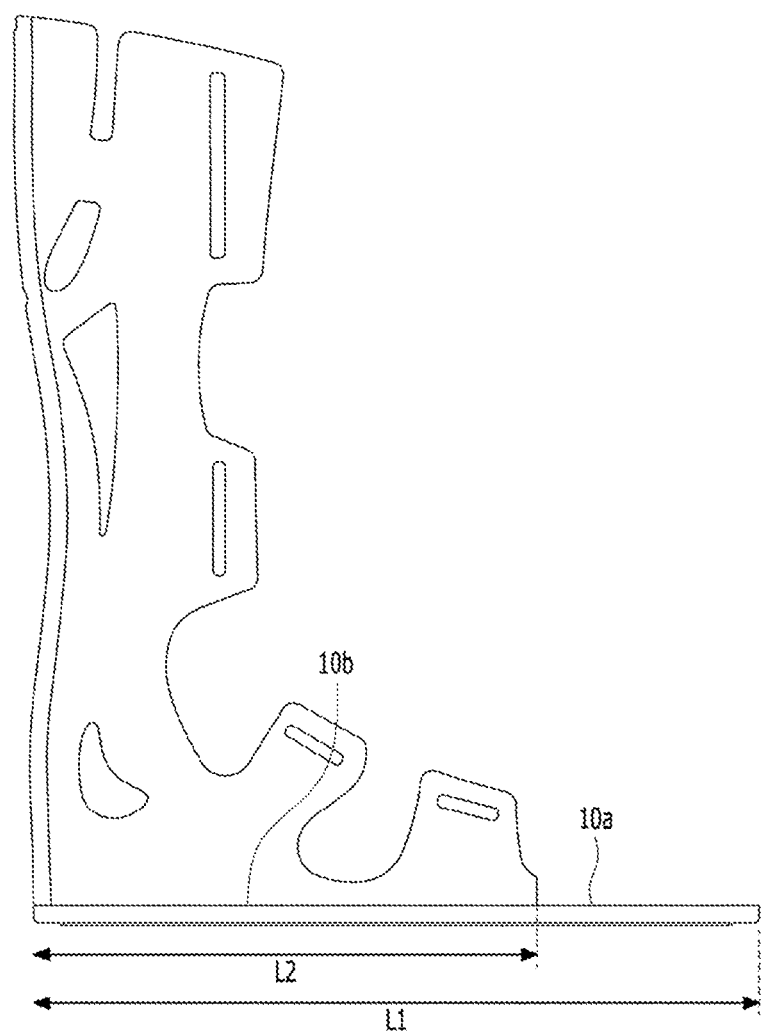
FIG. 7 is a side schematic view of the leg protector according to one embodiment of the present disclosure.
Figure 8:
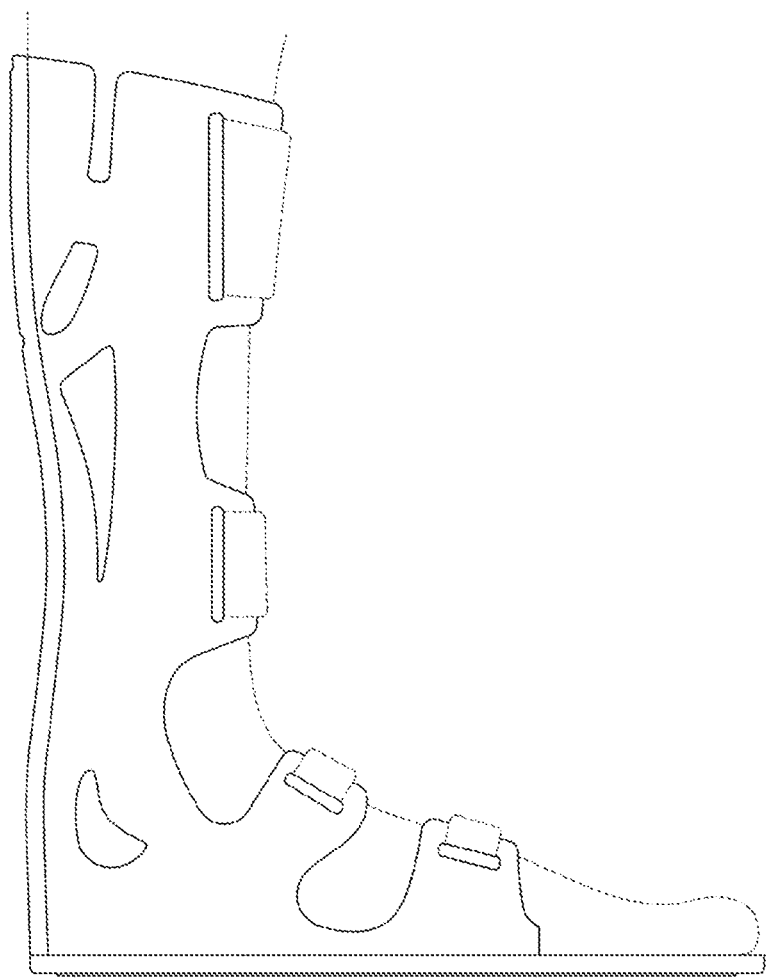
FIGS. 8 to 10 are side schematic views illustrating a state in which the leg protector according to one embodiment of the present disclosure is used.
Figure 9:
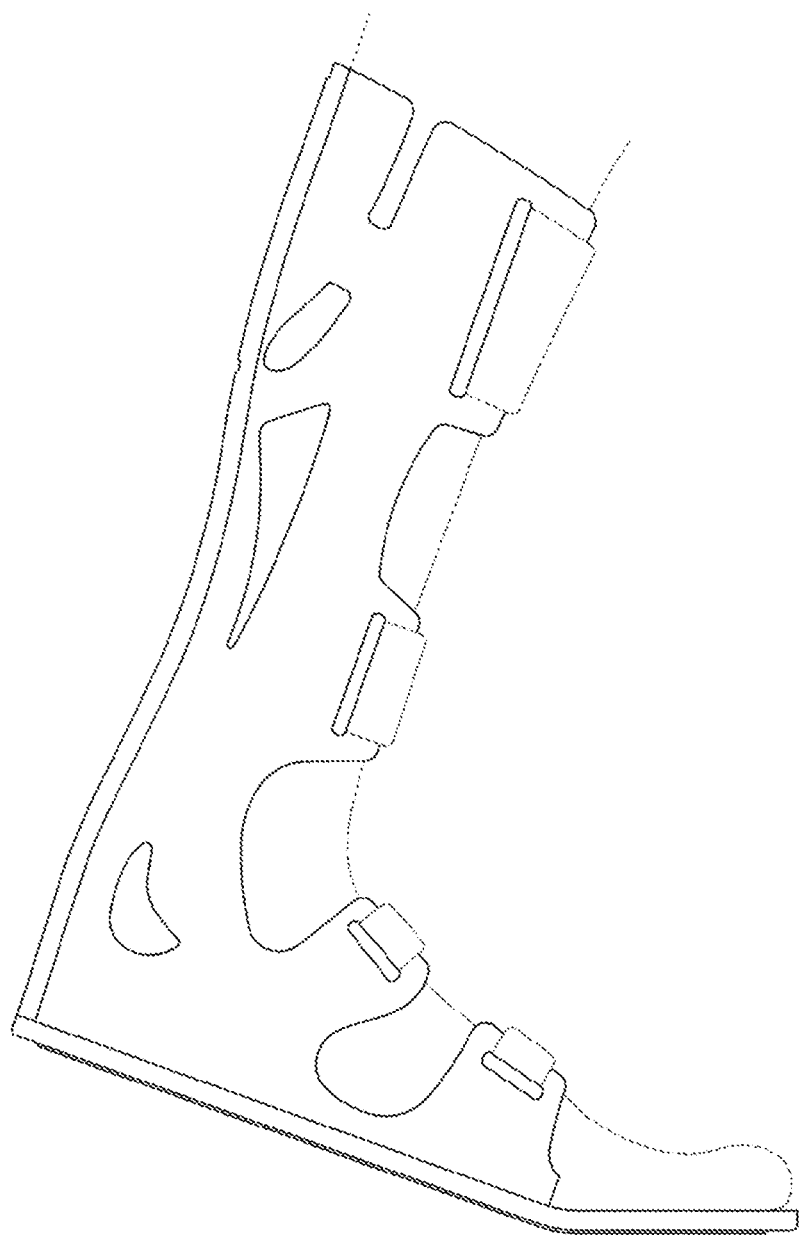
Figure 10:
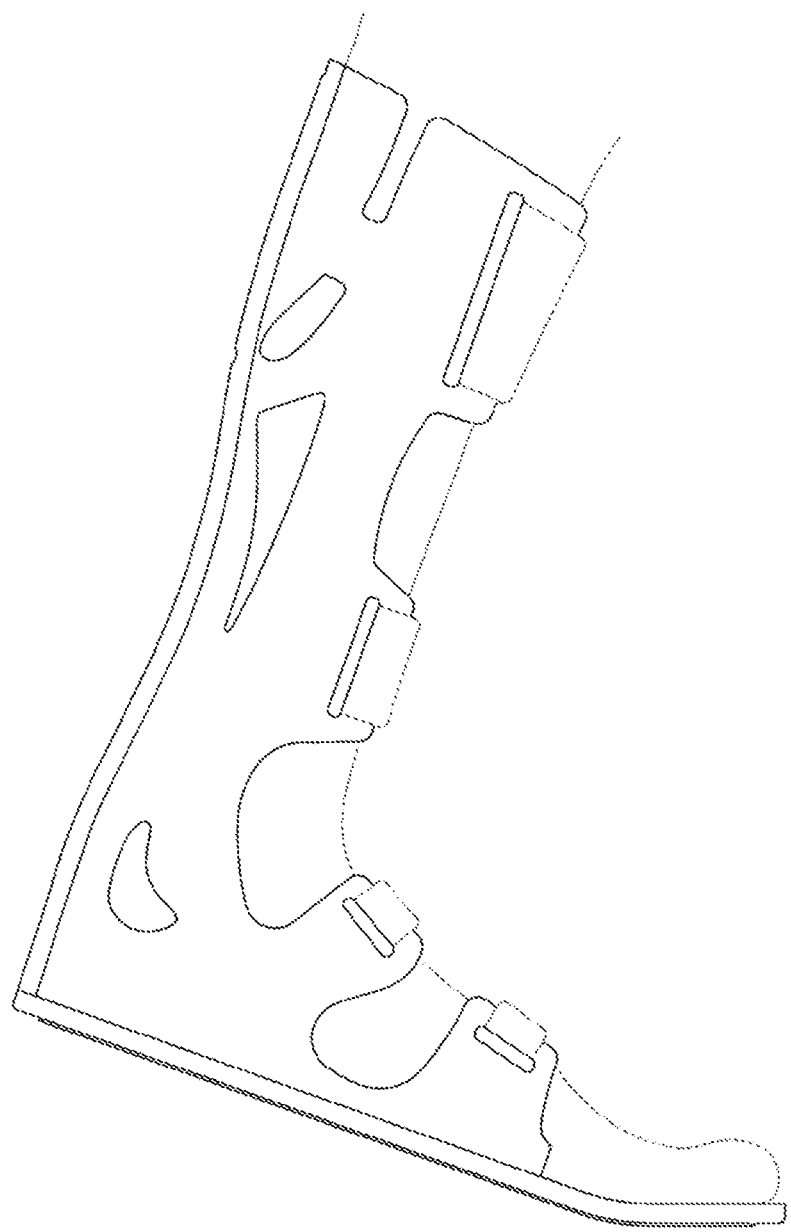

FIG. 7 is a side schematic view of the leg protector according to one embodiment of the present disclosure. FIGS. 8 to 10 are side schematic views illustrating a state in which the leg protector according to one embodiment of the present disclosure is used.

The bottom plate part 10 of the present embodiment includes a front bottom plate part 10a located at a front side of the foot and configured to not be connected to the protection part 20 for surrounding the lateral surface portion of the foot, and a rear bottom plate part 10b located at a rear side of the foot and connected to the protection part 20 for surrounding the lateral surface portion of the foot.

With such a configuration, elastic bending deformation of the bottom plate part 10 is generated by a walking weight of the wearer, and the front bottom plate part 10a is configured to generate elastic bending deformation that is greater than that of the rear bottom plate part 10b.

The fact that the front bottom plate part 10a generates elastic bending deformation that is greater than that of the rear bottom plate part 10b may mean that, although slight elastic bending deformation is also generated at the rear bottom plate part 10b due to the walking weight of the wearer, a case in which greater elastic bending deformation may be generated at the front bottom plate part 10a, or a case in which the elastic bending deformation may be generated at only the front bottom plate part 10a.

Such a deformation characteristic is resulting from a structure in which the front bottom plate part 10a is not connected to the protection part 20 and thus deformation of the bottom plate is easily generated when the walking weight is applied, while generation of bending deformation of the rear bottom plate part 10b is restricted due to the protection part 20 which is integrally connected to an edge of a lateral surface of the rear bottom plate part 10b. To this end, the protection part 20 of the present embodiment, particularly the foot protection plates 26a and 26a', is preferably formed to have a thickness and a physical property sufficient to restrict bending deformation of the rear bottom plate part 10b and is preferably formed to be connected to the bottom plate part 10b without discontinuity to a heel portion.

FIG. 8 illustrates a state in which a walking weight is not generated at the bottom plate part 10 because the wearer is in a stop state, and FIG. 9 or 10 illustrates a state in which elastic bending deformation is generated at the front bottom plate part 10a due to the walking weight when the wearer is walking. FIG. 9 illustrates a state in which deformation is generated at a substantially starting point of the front bottom plate part 10a which is not connected to the protection part 20, and FIG. 10 illustrates a state in which deformation is generated at a substantially intermediate point of the front bottom plate part 10a.

Owing to such elastic deformation, a structure in which, when the wearer is walking, the leg protector firmly fixes the leg and the ankle and partially allows a sole of the foot to move around a front portion of the foot is provided such that, when light injury such as a strain around the leg or the ankle occurs, the injured area may be protected and flexibility of the bottom plate around a toe joint portion may be secured, thereby allowing a patient may perform daily walking.

According to another aspect, it can be considered that the bottom plate part 10 has a first state (the state shown in FIG. 8) in which bending deformation is not generated and a second state (the state shown in FIG. 9 or 10) in which elastic bending deformation is generated at the front bottom plate part 10a due to a walking weight of the wearer, and the bottom plate part 10 is configured to provide a restoring force from the second state to the first state by the elastic bending deformation generated at the front bottom plate part 10a.

With such elastic deformation and such a restoration structure, when the wearer is walking, the wearer wearing the leg protector receives an auxiliary force for a smooth walking from the bottom plate part 10.

In order to facilitate the walking, the fastener engagement part of the present embodiment includes the first fastener engagement part 26c formed at each of the foot protection plates 26a and 26a' to fix the foot at a side of a dorsum pedis of the wearer around the opening 29, and the second fastener engagement part 26d formed at each of the leg protection plates 26b and 26b' to fix the leg at a front side of the leg of the wearer around the opening 29, and the fastener engagement part is configured to firmly fix the foot and the leg of the wearer.

Preferably, the foot protection plates 26a and 26a' are formed to extend from a rear end point of the bottom plate part 10 toward a front end point thereof in a position range of 63% to 73% of a straight foot length L1 in a front-rear direction.

A reference numeral L2 denotes a distance from the heel to a front end point of each of the foot protection plates 26a and 26a', and when the straight foot length L1 is 100%, each of the foot protection plates 26a and 26a' are formed such that L2 has a position range of 63% to 73% of the straight foot length L1.

According to the statistics released by Korean Agency for Technology and Standards (6th anthropometric survey, 2010), in the case of adult males and females of 30s to 50s, when a straight foot length is 100%, an average length between a heel and a point outside a foot (a joint starting point of a little toe) has a value corresponding to 63% of the straight foot length, and an average length between the heel and a point inside the foot (a joint starting point of a big toe) has a value corresponding to 73% of the straight foot length.

In consideration of the foregoing, a position of a toe joint may be in a position range of 63% to 73% from the heel. Therefore, when a starting point of the front bottom plate part 10a requiring generation of elastic bending deformation is formed in the same position range, the wearer may secure a position of the elastic bending deformation according to the position of the toe joint to perform a smooth walking.

Figure 11:
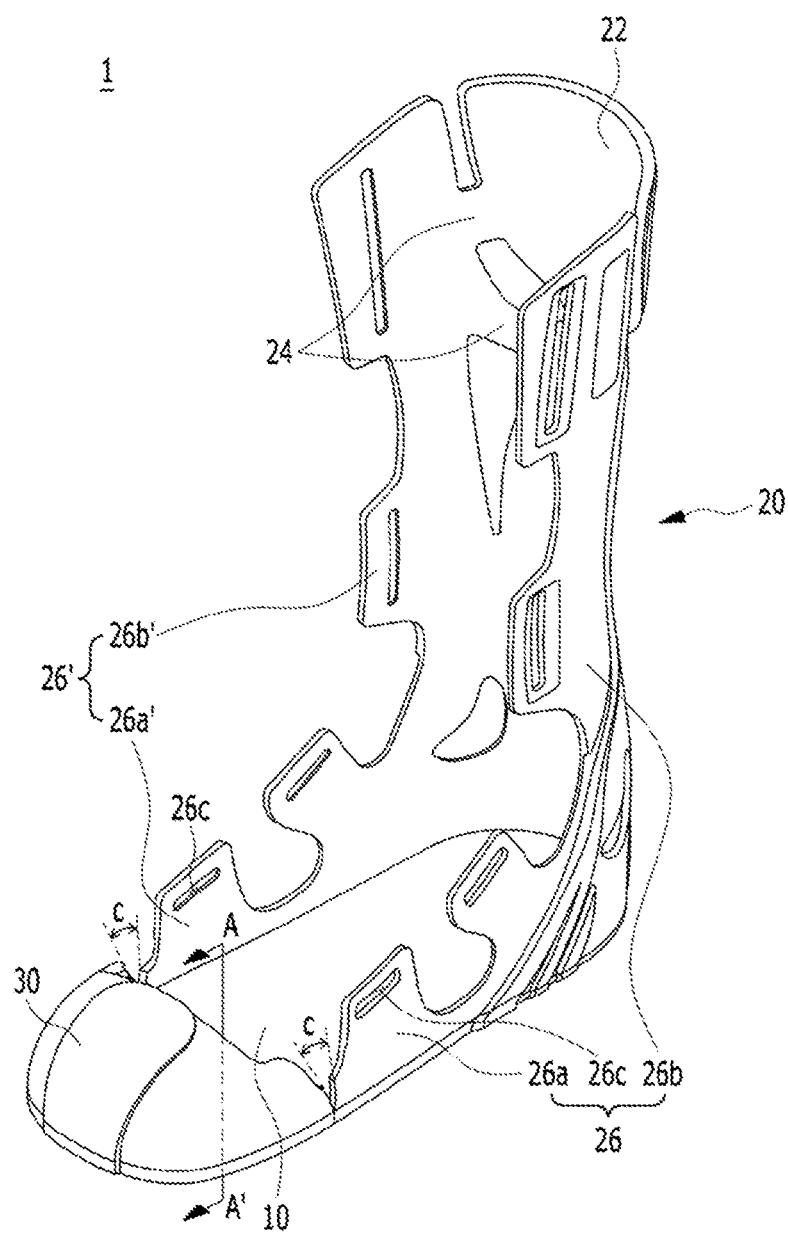
FIG. 11 is a perspective view of a leg protector according to another embodiment of the present disclosure.

FIG. 11 is a perspective view of a leg protector according to another embodiment of the present disclosure.

As described above, the toe cover part 30 may be provided at the leg protector of the present embodiment. In the present embodiment, in order to easily generate elastic bending deformation even when the toe cover part 30 is provided, a gap C is formed at the protection part 20, particularly at each of mutual adjacent portions between the toe cover part 30 and the left and right foot protection parts 26a and 26a'.

With such a configuration, even when elastic bending deformation is generated at the front bottom plate part 10a while the wearer wears the leg protector of the present embodiment to walk, the toe cover part 30 and the left or right foot protection parts 26a and 26a do not interfere by the gaps C such that the wearer is able to perform a smooth walking.

Figure 12:
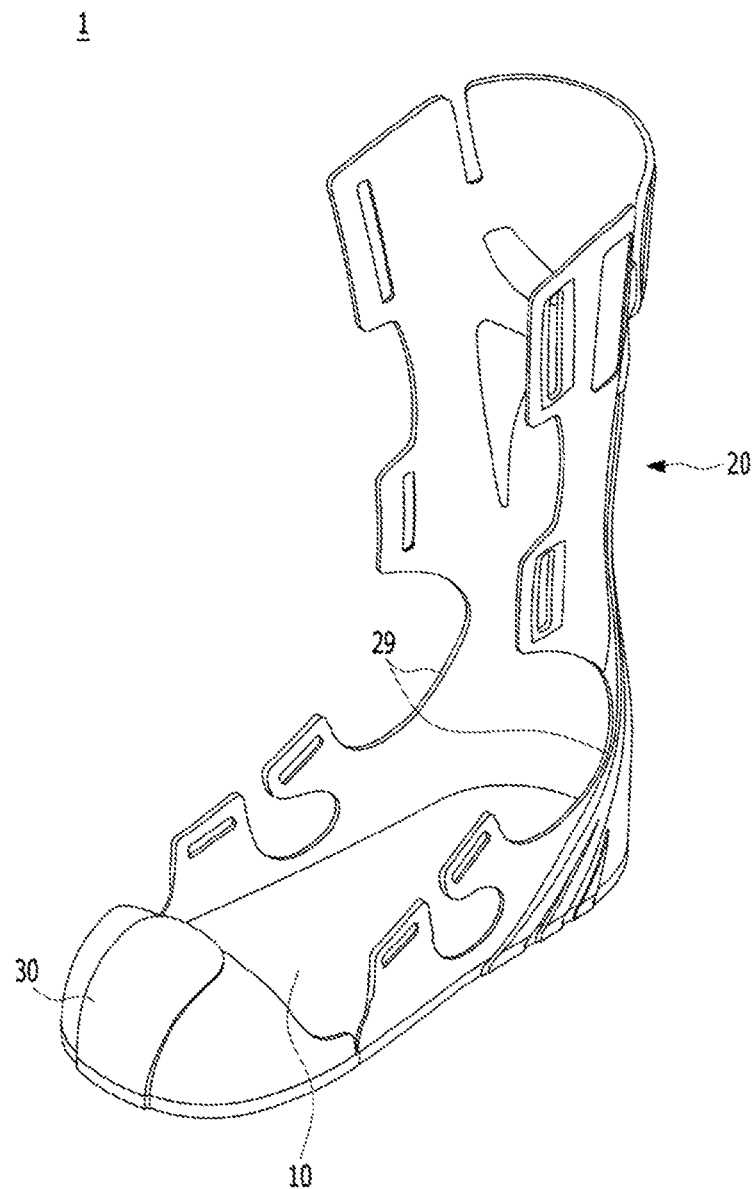
FIG. 12 is a perspective view of a leg protector according to still another embodiment of the present disclosure.

FIG. 12 is a perspective view of a leg protector according to still another embodiment of the present disclosure.

The leg protector of the present embodiment is a modification of the embodiments of FIGS. 1 to 6 and has a form in which an area of the opening 29 is formed to be relatively larger compared with the embodiments of FIGS. 1 to 6, thereby increasing convenience when the leg protector is detached and reducing pressure at a portion adjacent to a malleolus of the wearer. In the present embodiment, in consideration of ventilation of a heel portion, which is relatively improved through the opening 29 which is formed to extend, the air hole 23 (FIG. 6) of the protection part 20 is omitted.

As described above, the leg protector of the present embodiment may have a partially deformed structure within a range maintaining the above-described basic characteristics. A walking weight analysis simulation, which will be described below, is performed with the model of the embodiment of FIG. 12.

Figure 13:
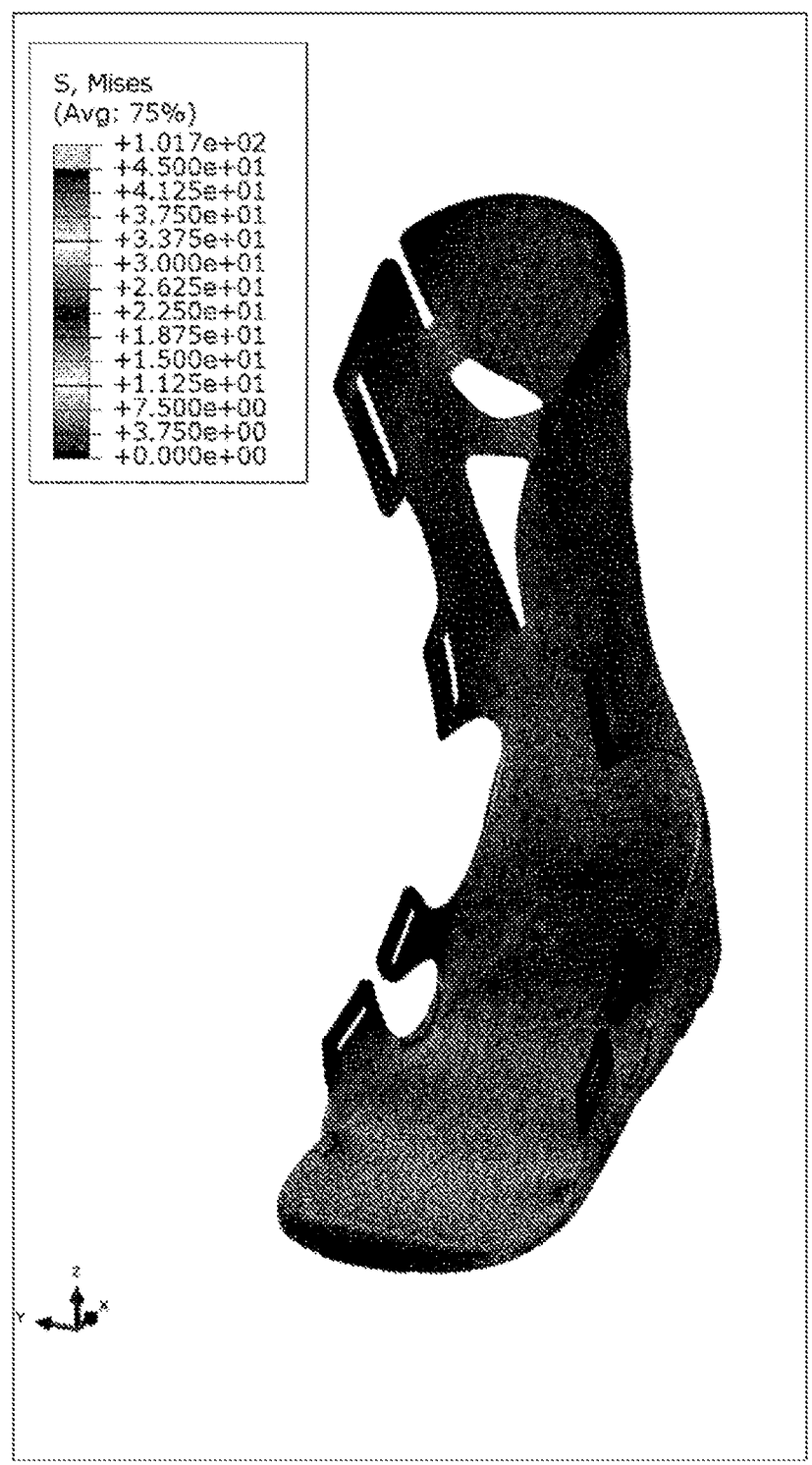
FIG. 13 is a screen shot of a walking weight analysis simulation of the leg protector according to one embodiment of the present disclosure.
Figure 14:
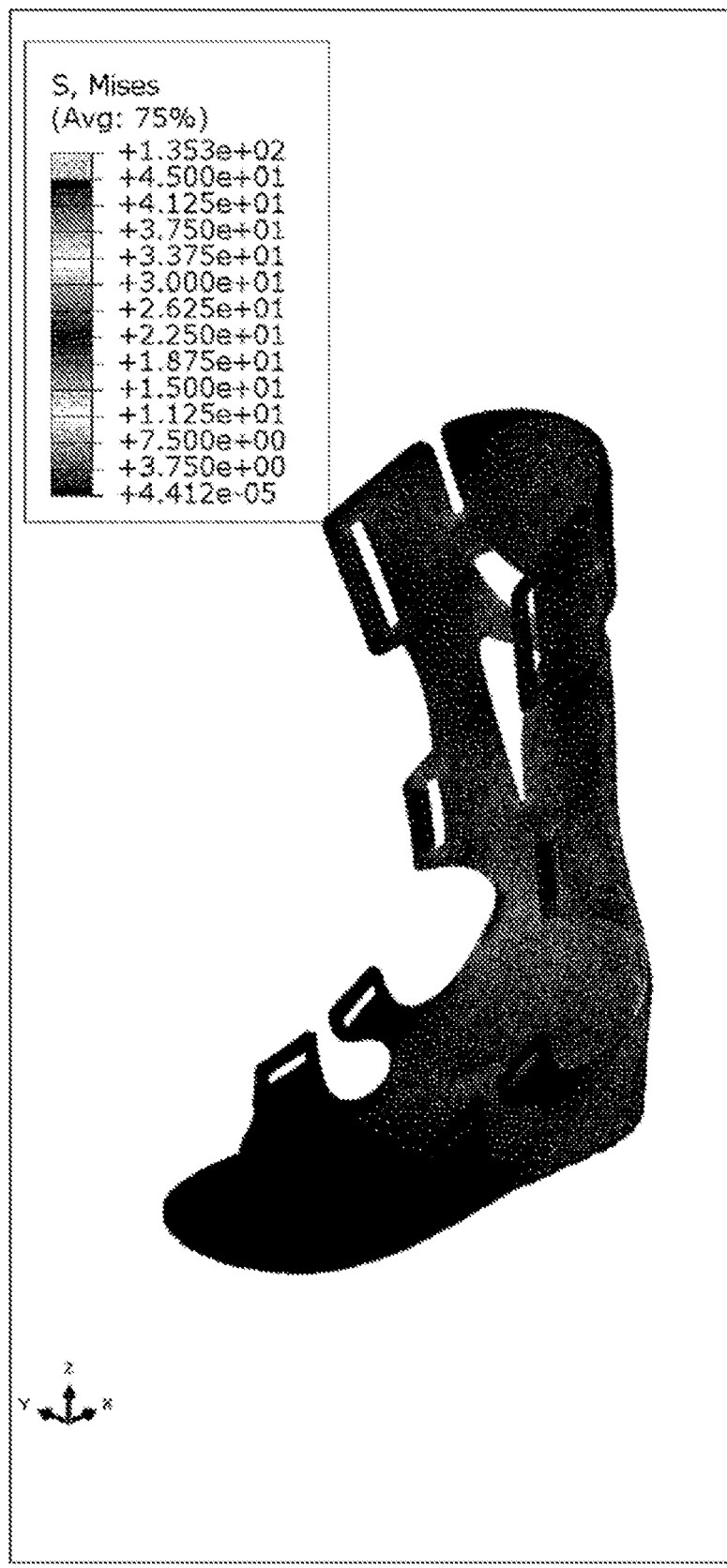
FIG. 14 is a screen shot of a walking weight analysis simulation of a leg protector according to Comparative Example.

FIG. 13 is a screen shot of a walking weight analysis simulation of the leg protector according to one embodiment of the present disclosure. FIG. 14 is a screen shot of a walking weight analysis simulation of a leg protector according to Comparative Example.

The walking weight load analysis simulation was performed using physical property data of a nylon resin (product name: TEKAMID TB120ST PA6). Detailed conditions of the physical property data are such that Rockwell hardness R was set to 105, tensile strength was set to 48 MPa, elongation at break was set to 150%, flexural yield strength was set to 45 MPa, and flexural modulus was set to 1.4 GPa. On the basis of the above-described physical property data, it was assumed that the model was an elastic-perfectly plastic model and it was analyzed using a finite element analysis method.

A height of the leg protector was set to 303 mm and the leg protector was assumed to be firmly fixed by the fastener 90 in a state in which the foot and the leg are inserted into the leg protector.

An example of FIG. 13 illustrates a case (similar to the state shown in FIG. 10) in which, when a walking weight is applied in a state in which the leg is inclined by 20 degrees toward the front side, a condition is given such that only the front bottom plate part 10*a* is kept in a landing state on the ground and thus bending deformation is generated due to the walking weight, and an example of FIG. 14 illustrates a case (a state in which only the protection part is inclined to the front side in FIG. 8) in which, when the same walking weight is applied, a condition is given such that the entire bottom plate part 10 is kept in the landing state on the ground and thus bending deformation is not generated at the bottom plate part 10.

In FIG. 13, it is confirmed that deformation is concentrated on the front bottom plate part 10*a*, and slight deformation is generated at the opening 29 and a partial intermediate portion of the rear bottom plate part 10*b*.

In FIG. 14, it is confirmed that deformation is not generated at the front bottom plate part 10*a* and the rear bottom plate part 10*b* and is concentrated on the opening 29.

Referring to such analysis results, the leg protector of the present embodiment provides a structure of firmly fixing the leg and the ankle and partially allowing a movement of the sole such that it is confirmed that the leg protector is effective for light injury such as a strain around the leg or the ankle.

Figure 15:
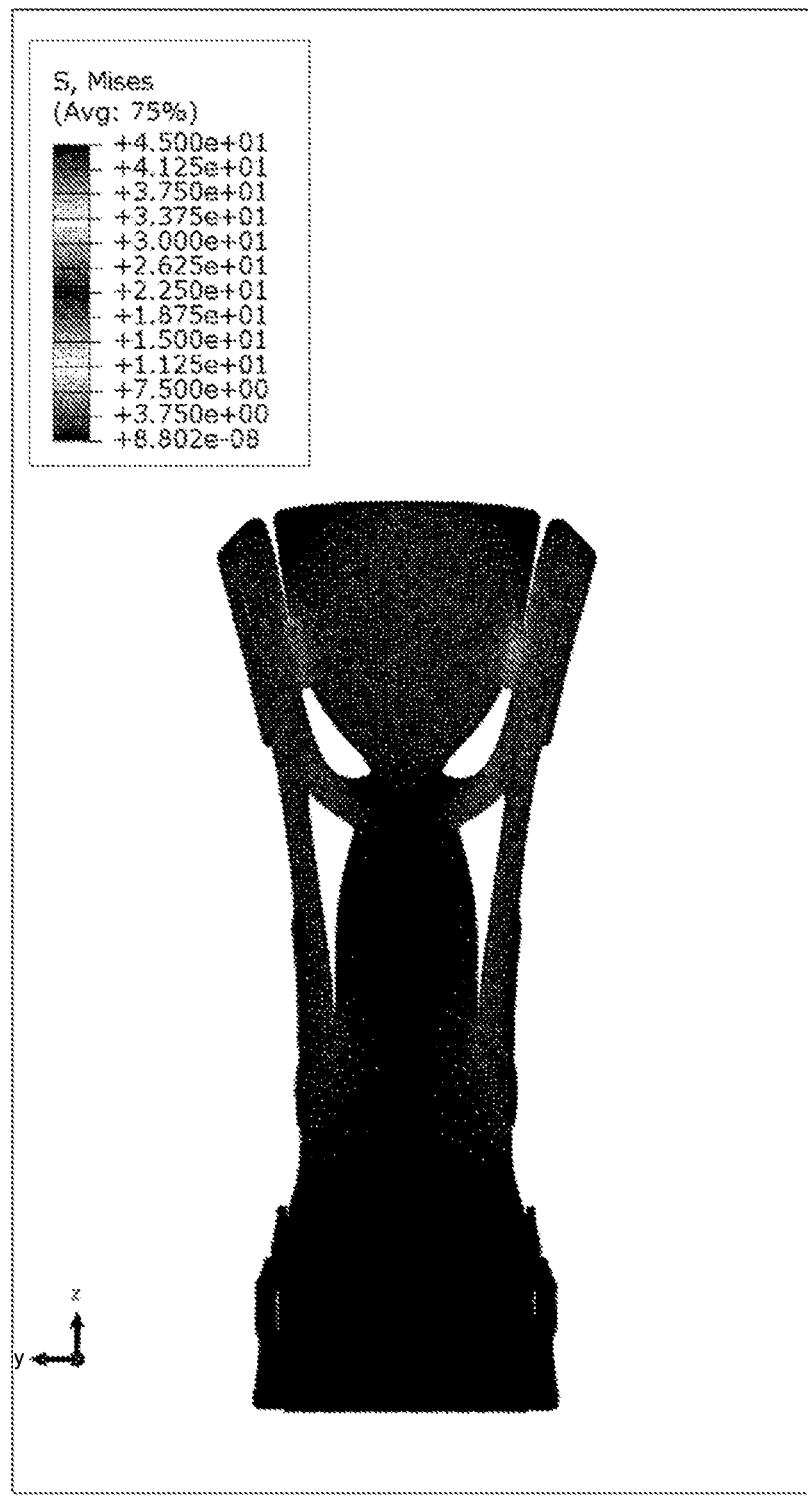
FIG. 15 is a screen shot of an analysis simulation of a lateral plate portion of the leg protector according to one embodiment of the present disclosure.
Figure 16:
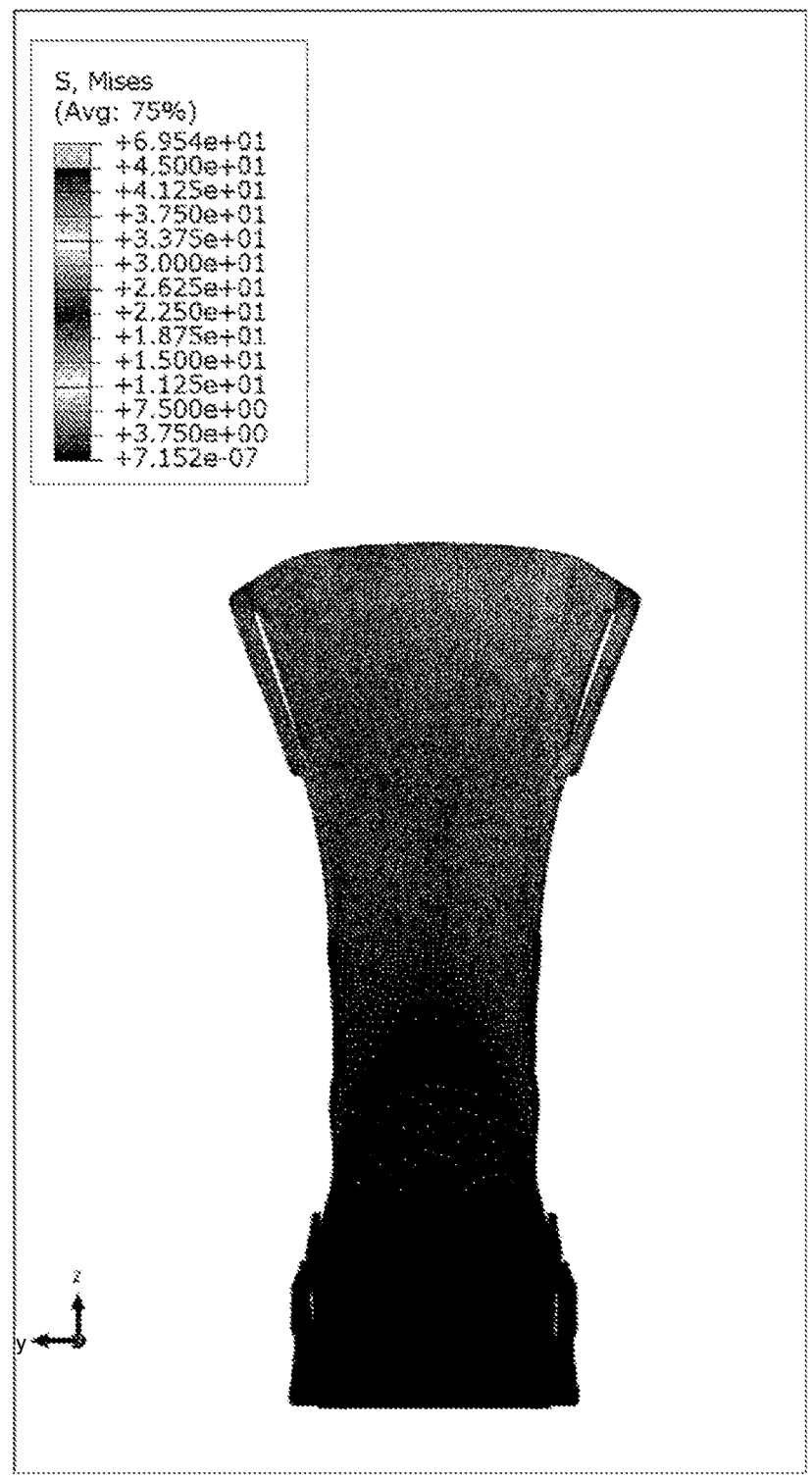
FIG. 16 is a screen shot of an analysis simulation of a lateral plate portion of a leg protector according to Comparative Example.

FIG. 15 is a screen shot of an analysis simulation of a lateral plate portion of the leg protector according to one embodiment of the present disclosure. FIG. 16 is a screen shot of an analysis simulation of a lateral plate portion of a leg protector according to Comparative Example.

A walking weight analysis simulation of FIGS. 15 and 16 was performed under the same analysis conditions as the simulations of FIGS. 13 and 14, except that the walking weight was not applied and a displacement condition was given such that, in a state in which the bottom plate part is completely restricted, one point of an upper end portion of each of the left leg protection plate 26*b* and right leg protection plate 26*b*' is pushed outward by 20 mm.

An example of FIG. 15 illustrates a case in which the left leg protection plate 26*b* and the right leg protection plate 26*b*' are separately formed to be connected through the first connector 24, and an example of FIG. 16 illustrates a case in which the left leg protection plate and the right leg protection plate are integrally formed without being separated.

In FIG. 15, it is confirmed that deformation is concentrated on only the first connector 24, and deformation is hardly generated at the left leg protection plate 26*b*, the right leg protection plate 26*b*', and the rear plate 22.

In FIG. 16, it is confirmed that deformation is generated across an entire area of the upper end portions of the left leg protection plate and the right leg protection plate which are integrally formed with the rear plate.

Referring to such analysis results, it can be seen that the leg protector of the present embodiment adaptively provides a widening effect through the first connector while a thickness of the leg is varied and during a wearing process.

Figure 17:
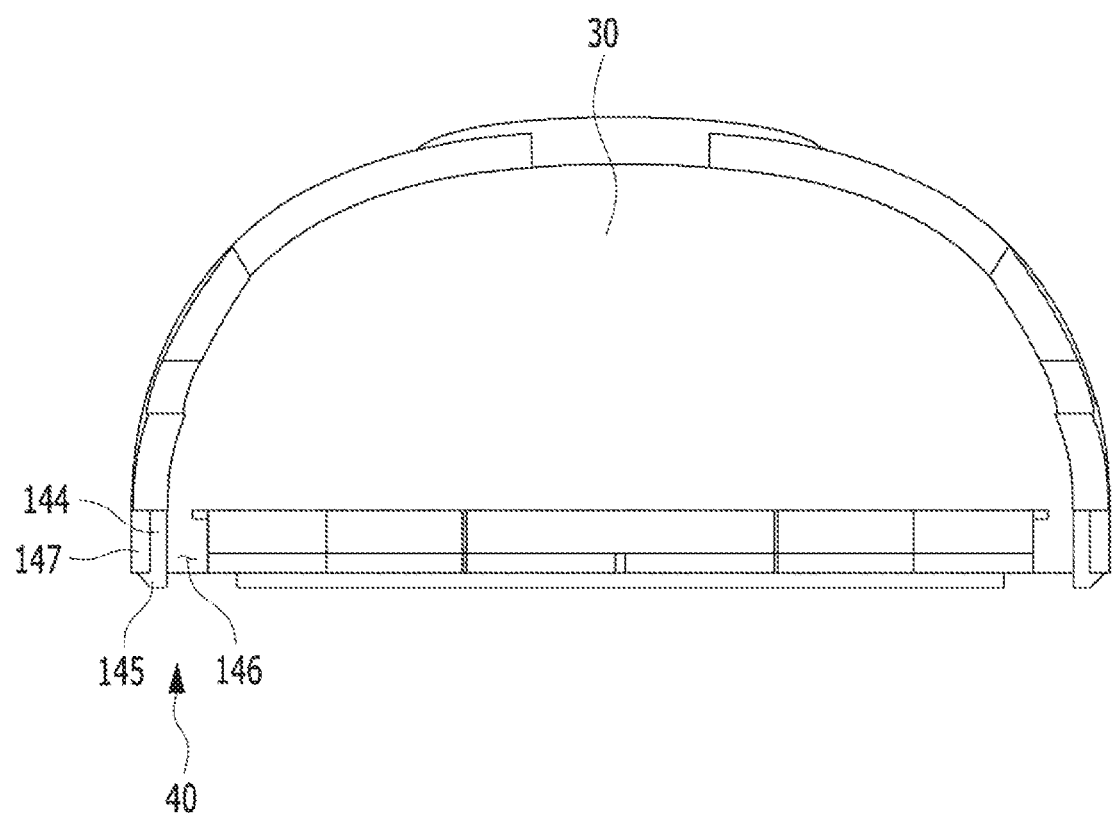
FIG. 17 is a cross-sectional view of a leg protector according to yet another embodiment of the present disclosure.

FIG. 17 is a cross-sectional view of a leg protector according to yet another embodiment of the present disclosure. A cover according to the present embodiment has a hook structure different from that of FIG. 3.

The detachable coupling part 40 according to yet another embodiment of the present disclosure includes at least one elastic insertion piece 144 formed at an end portion of the cover 32 and an insertion hole 146 formed at a position of the bottom plate part 10 corresponding to the elastic insertion piece 144.

The elastic insertion piece 144 is formed to extend downward and includes a hook part 145 having one end connected to the end portion of the cover 32, and the other end exposed to a lower side of the insertion hole 146 and hooked to a hook bump 147 provided at one lateral surface of the insertion hole 146.

With such a hook structure, the elastic insertion piece 144 and the hook part 145 have a more simplified structure such that there is an advantage in which a hook coupling may be made more rigid.

Preferably, the elastic insertion piece 144 of the present embodiment may be formed at each of left and right end portions of the cover 32.

Meanwhile, the detachable part 145 of the present embodiment is formed to be exposed to the downward side through the insertion hole 146 of the bottom plate part 10 in a state of being coupled such that the wearer may operate the detachable part 145 at the lower side of the bottom plate part 10. In consideration of the foregoing, the elastic insertion piece 144 of the present embodiment may be preferably located not only at the left side and right end portions of the cover 32 but also at a central front end portion thereof at which the toes are located.

When the elastic insertion piece 144 is located at the central front end portion of the cover 32, there is an advantage in that a coupling state is firmly made even to the front side of the cover 32.

Meanwhile, as described above with reference to FIG. 11, a gap C is formed at the protection part 20, particularly at each of mutual adjacent portions between the toe cover part 30 and the left and right foot protection parts 26*a* and 26*a*'.

With such a configuration, even when bending deformation is generated at the front bottom plate part 10*a* while the wearer wears the leg protector of the present embodiment to walk, there is an advantage in that the toe cover part 30 and the left and right foot protection parts 26*a* and 26*a* are in a smooth contact state the gaps C.

Figure 18:
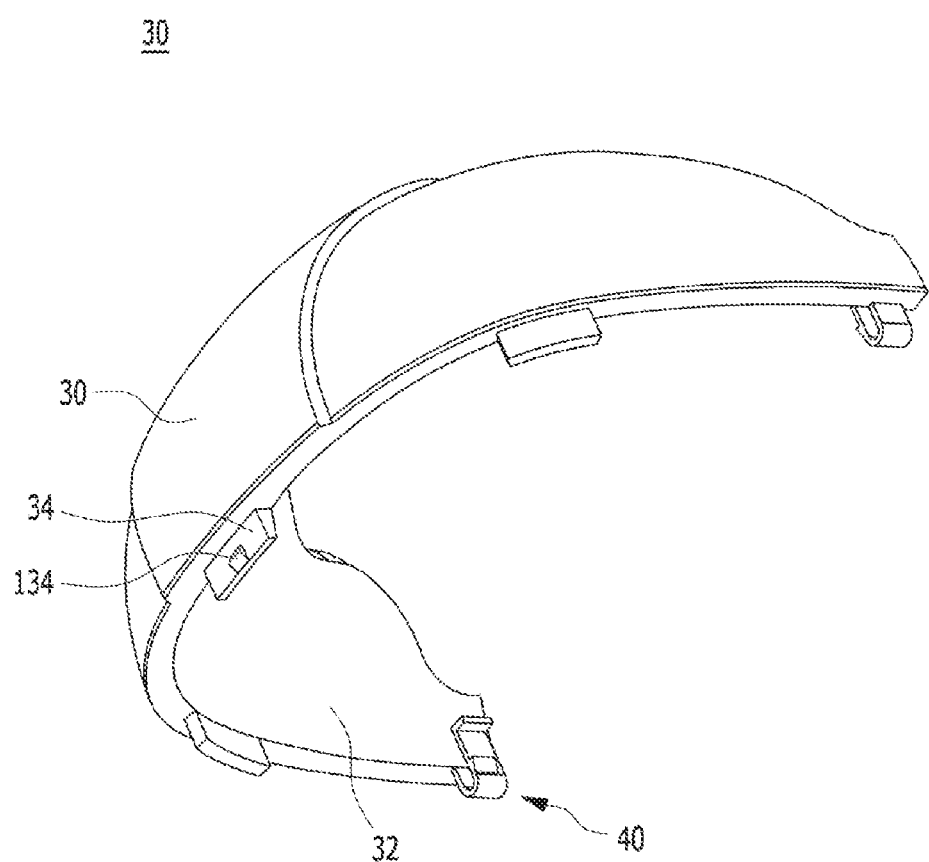
FIG. 18 is a perspective view of a toe lid part of the leg protector according to yet another embodiment of the present disclosure.
Figure 19:
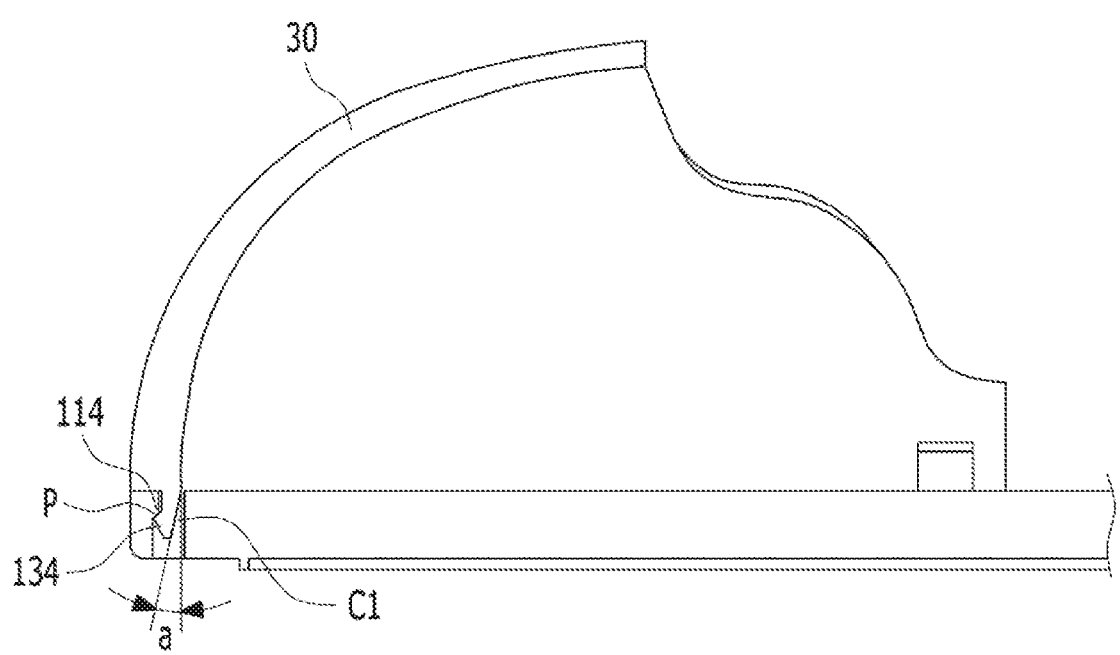
FIG. 19 is a partial cross-sectional view of the toe lid part of the leg protector according to yet another embodiment of the present disclosure.
Figure 20:
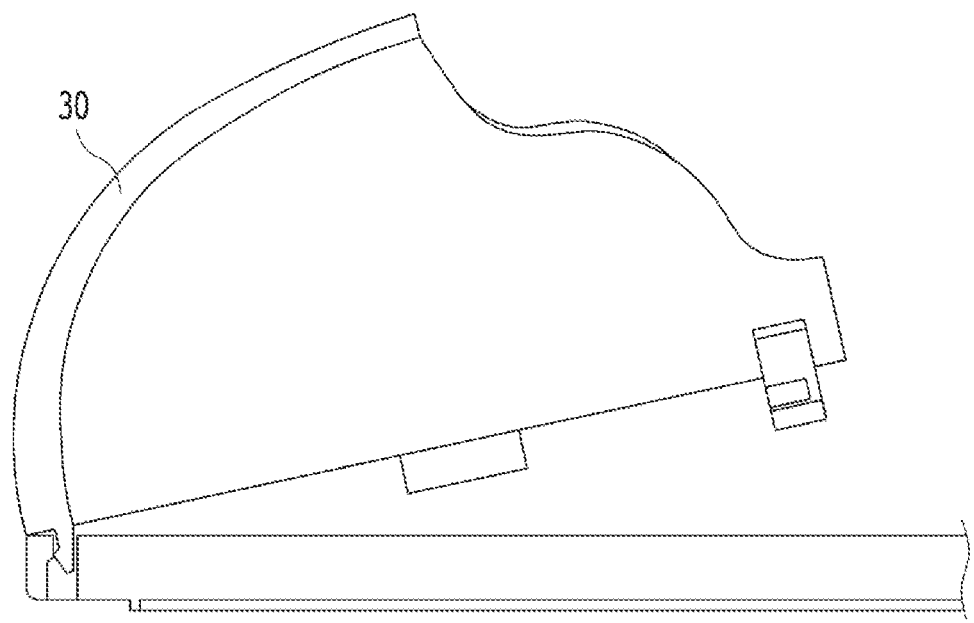
FIG. 20 is a partial cross-sectional view illustrating a state in which a cover engagement part of a protruding insertion piece is released from a cover engagement bump of a recess in a state shown in FIG. 19.

FIG. 18 is a perspective view of a toe lid part of the leg protector according to yet another embodiment of the present disclosure. FIG. 19 is a partial cross-sectional view of the toe lid part of the leg protector according to yet another embodiment of the present disclosure. FIG. 20 is a partial cross-sectional view illustrating a state in which a cover engagement part of a protruding insertion piece is released from a cover engagement bump of a recess in a state shown in FIG. 19. FIG. 19 is a cross-sectional view taken along the line C-C of FIG. 1. An overlapping description of a configuration the same as the above-described configuration will be omitted.

A leg protector 1 according to still another embodiment of the present disclosure has the above-described basic configuration of FIGS. 1 to 6 and is configured to couple the cover 32 to the bottom plate part 10 more firmly.

To this end, one or more protruding insertion pieces 34 are formed at one side of the end portion of the cover 32, and the recess 14 into which the protruding insertion piece 34 is insertable is formed at a position of the bottom plate part 10 corresponding to each of the one or more protruding insertion pieces 34.

Further, a cover engagement part 134 is provided at a lower end of the protruding insertion piece 34 to be inserted into a lower side of the recess 14 in a state of being coupled and to be hooked to a cover engagement bump 114 formed at the lower side of the recess 14.

In the present embodiment, it is exemplified a case such that the cover engagement part 134 is formed at the front side (a front side of the toe) of the lower end of the protruding insertion piece 34. Alternatively, the protruding insertion piece 34 may be formed at the rear side (a side of the sole) of the lower end of the protruding insertion piece 34.

With such a configuration, a coupling between the cover 32 and the bottom plate part 10 is made more firmly, and when the wearer is walking, it is possible to prevent the protruding insertion piece 34 of the cover 32 from being unintentionally separated from the recess 14.

As shown in FIG. 2, a plurality of protruding insertion pieces 34 may be formed along the end portion of the cover 32, and alternatively, a single protruding insertion piece 34 may be formed at a foremost end of the cover 32 (a foremost end of a central portion of the toes).

More preferably, the protruding insertion piece 34 is formed to be located at a foremost end portion of the cover 32 (the foremost end of the central portion of the toes). Consequently, as described below, when the cover 32 is pivoted and opened, the protruding insertion piece 34 located at the foremost end portion of the cover 32 may be used as a pivoting center.

Further, in order to allow the detachable coupling part 40 to be released and to be pivoted and opened upward about the protruding insertion piece 34 at which the cover 32 is located at the foremost end portion, the gap C1 is formed between the recess 34 and the protruding insertion piece 34 located at the foremost end portion of the cover 32.

The gap C1 may be provided by forming a slight gap at least one side of surfaces facing each other of the protruding insertion piece 34 or the recess 14 or by forming an inclined surface thereat.

Through such a gap C1, the cover 32 is capable of being smoothly pivoted and opened upward about the protruding insertion piece 34 located at the foremost end portion.

Further, in a state in which the detachable coupling part 40 is released and the cover 32 is pivoted and opened upward about the protruding insertion piece 34 located at the foremost end portion, the cover engagement part 134 of the protruding insertion piece 34 and the cover engagement bump 114 of the recess 14 are formed to be in a hook release state.

For example, when the surfaces facing each other of the protruding insertion piece 34 and the cover engagement bump 114 are respectively formed in an inclined surface shape having inclination from perpendicularity, and an inclined surface having an angle similar to an angle of the inclined surface shape is formed between an inner surface of the protruding insertion piece 34 opposite the cover engagement part 134 and the recess 14 facing the inner surface, in a state in which the cover 32 is pivoted and opened upward about the protruding insertion piece 34 located at the foremost end portion, a hook P between the cover engagement part 134 and the engagement bump 114 may be naturally released such that a separation manipulation may be easily performed. Such a state is illustrated in FIG. 20.

With such a configuration, the wearer merely releases the detachable coupling part 40 and pivots to open upward the cover 32 about the protruding insertion piece 34 located at the foremost end portion of the cover 32 such that the separation between the cover 32 and the bottom plate part 10 may be easily performed.

Figure 21:
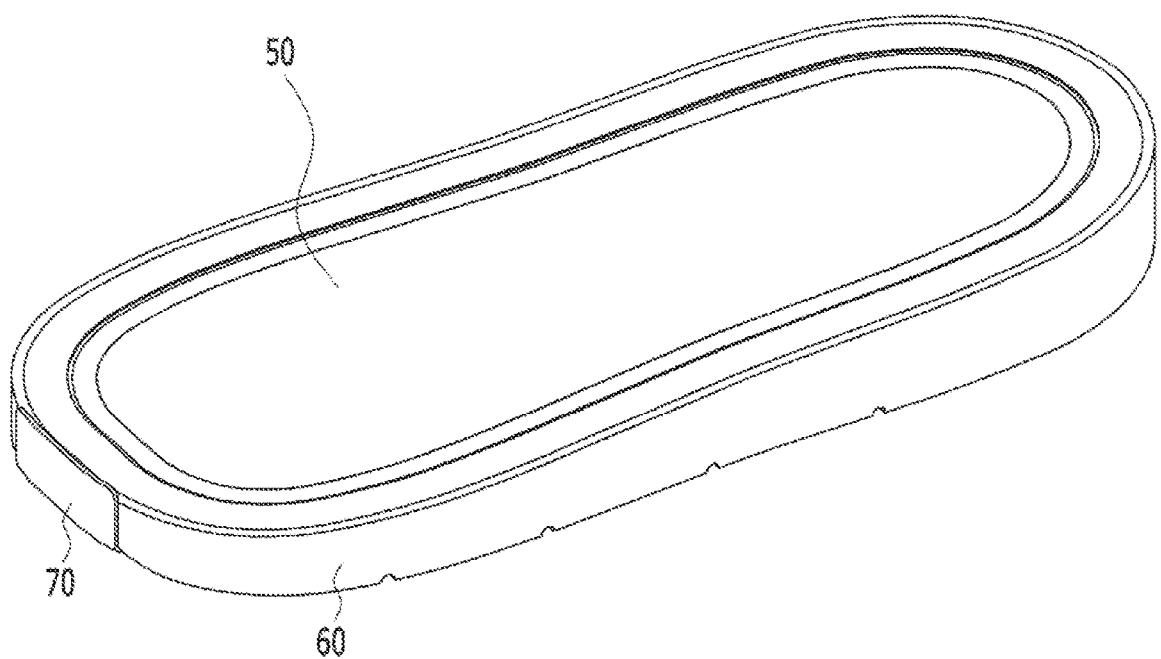
FIG. 21 is a perspective view of a sole portion of the leg protector according to yet another embodiment of the present disclosure.
Figure 22:
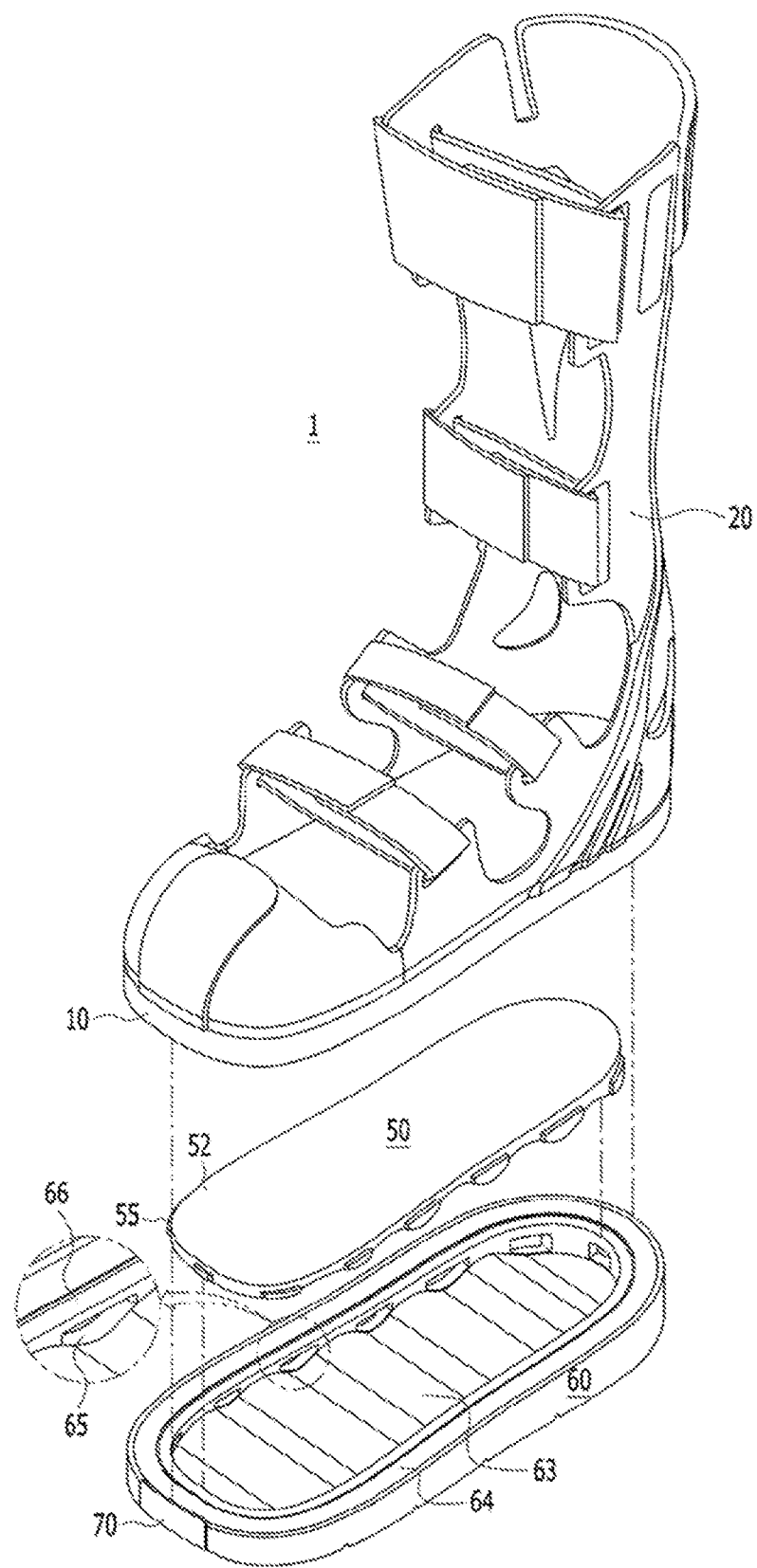
FIG. 22 is an exploded perspective view of a sole portion of the leg protector according to yet another embodiment of the present disclosure.
Figure 23:
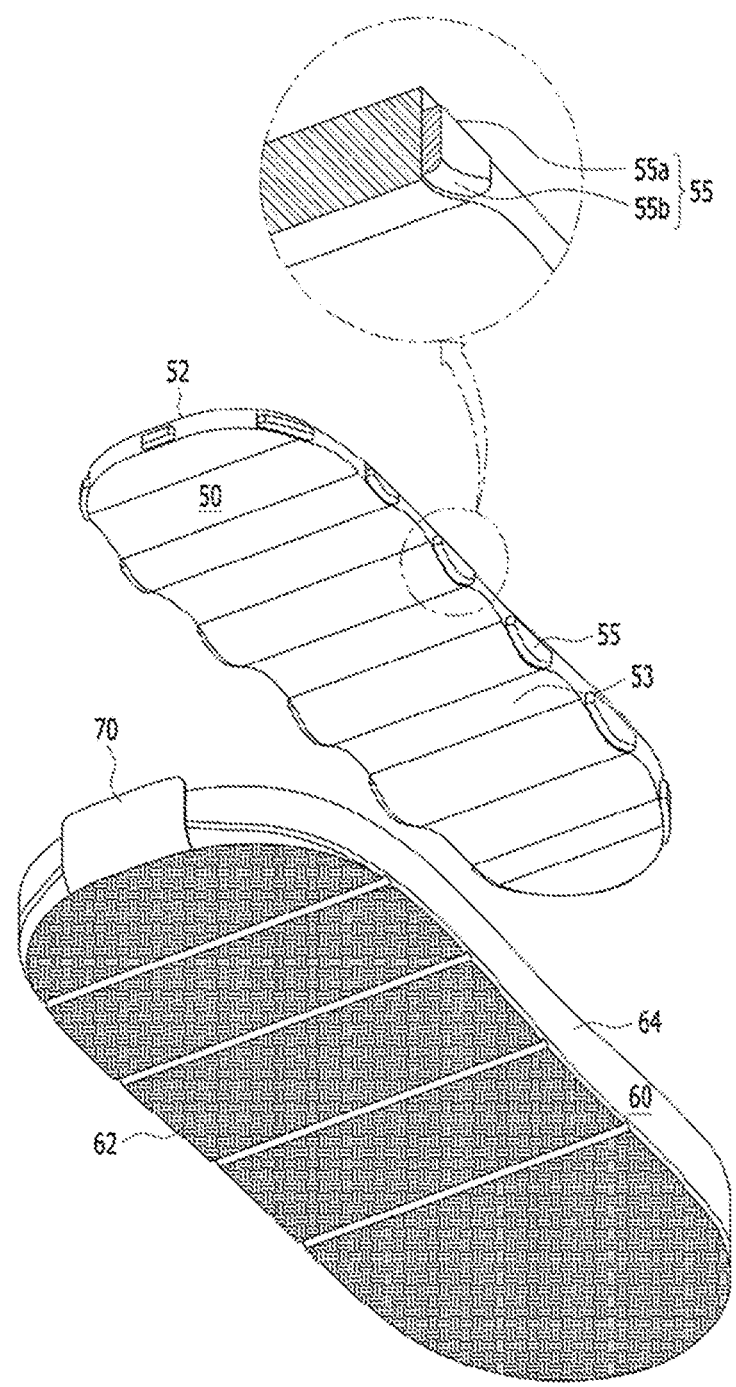
FIG. 23 is an exploded perspective view of the sole portion of the leg protector according to yet another embodiment of the present disclosure when viewed from another direction.
Figure 24:
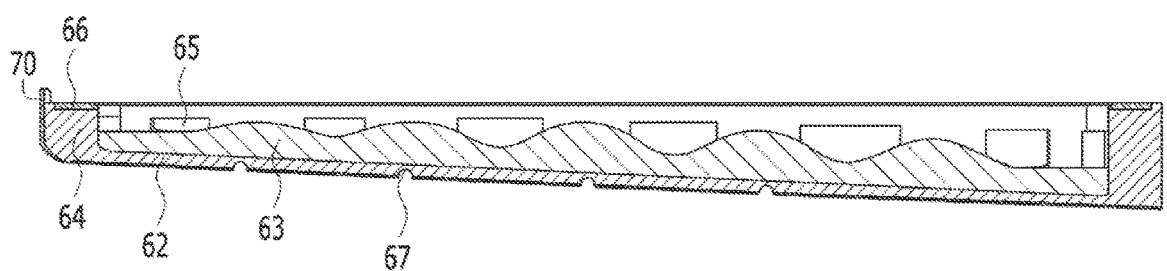
FIG. 24 is a cross-sectional view of a second sole according to yet another embodiment of the present disclosure.

FIG. 21 is a perspective view of a sole portion of the leg protector according to yet another embodiment of the present disclosure. FIG. 22 is an exploded perspective view of a sole portion of the leg protector according to yet another embodiment of the present disclosure. FIG. 23 is an exploded perspective view of the sole portion of the leg protector according to yet another embodiment of the present disclosure when viewed from another direction. FIG. 24 is a cross-sectional view of a second sole according to yet another embodiment of the present disclosure. An overlapping description of a configuration the same as the above-described configuration will be omitted.

The leg protector 1 according to the present embodiment of the present disclosure includes the bottom plate part 10 for supporting a foot, the protection part 20 for fixing and protecting the foot and a leg, a first sole 50, and a second shoe sole 60. The second shoe sole 60 can be considered as an element identical to the shoe sole 60 of FIG. 6.

The first sole 50 is provided at a lower side of the bottom plate part 10.

The first sole plate 50 according to the present embodiment includes a first sole plate part 52 having a first curved part 53 which is provided at a lower surface of the first sole plate part 52 and at which a plurality of curves are disposed in a front-rear direction of the foot, and a plurality of lateral protrusions 55 formed along a lateral surface of the first sole plate part 52.

Preferably, the first sole plate part 52, the first curved part 53, and the plurality of lateral protrusions 55 may be integrally formed by. e.g., injection molding using a mold.

The second shoe sole 60 is detachably coupled to a lower side of the first sole 50.

The second shoe sole 60 according to the present embodiment includes a second sole plate part 62 having a second curved part 63 formed in a curved shape corresponding to a shape of the first curved part 53 at an upper surface of the second sole plate part 62, a protrusion insertion recess 65 configured to allow each of the plurality of lateral protrusions 55 to be insertable into the protrusion insertion recess 65, and a lateral wall 64 formed along an edge of the second sole plate part 62.

Preferably, the second sole plate part 62, the second curved part 63, the protrusion insertion recess 65, and the lateral wall 64 are integrally formed by, e.g., injection molding using a mold frame.

The first curved part 53 and the second curved part 63 fix a position when the first sole 50 and the second shoe sole 60 are coupled, and the lateral protrusion 55 and the protrusion insertion recess 65 allow and maintain a coupling between the first sole 50 and the second shoe sole 60.

The first sole 50 and the second shoe sole 60 are preferably made of stretchable material. For example, ethylene-vinyl acetate (EVA), urethane, polyurethane (PU), a foam sponge, rubber, and the like may be used.

The first curved part 53 and the second curved part 63 are formed in corresponding curved shapes so that corresponding portions of the first curved part 53 and the second curved part 63 are coupled by being in surface contact with each other.

The curved shape of each of the first curved part 53 and the second curved part 63 is preferably formed in a rounded shape.

The curved shape is formed in a rounded shape such that a coupling between the first sole 50 and the second shoe sole 60 is easily performed.

In other words, even in a state in which the first sole 50 is not exactly placed at the same position on the upper portion of the second shoe sole 60, when the first sole 50 and the second shoe sole 60 are placed at appropriate similar positions in the front-rear direction of the foot of the wearer wearing the leg protector 1 according to the present embodiment and then the first sole 50 is pressed downward, the curved shape of the first curved part 53, which is formed in a rounded shape, smoothly slides on the curved shape of the second curved part 63 to be fit to an accurate position such that the first sole 50 and the second shoe sole 60 are easily coupled.

Accordingly, in a state in which the wearer wears the leg protector 1 according to the present embodiment, the wearer merely applies downward an appropriate force by placing the first sole 50 provided at the lower portion of the bottom plate part 10 on the second shoe sole 60 such that an insertion coupling between the second shoe sole 60 and the first sole 50 may be performed.

As described above, the insertion coupling is maintained by inserting the lateral protrusion 55 into the protrusion insertion recess 65.

That is, when the first sole 50 and the second shoe sole 60 are inserted and coupled, the lateral wall 64 of the second shoe sole 60 is opened outward due to the lateral protrusion 55 and are in surface contact with each other at a position at which the first curved part 53 and the second curved part 63 correspond to each other, and simultaneously, the lateral wall 64 is pressed inward by an elastic force applied to the lateral wall 64 such that the insertion of the lateral protrusion 55 is inserted into the protrusion insertion recess 65.

In order to maintain the coupling between the lateral protrusion 55 and the protrusion insertion recess 65, the lateral protrusion 55 and the protrusion insertion recess 65 are preferably formed to have similar shapes and dimensions (e.g., areas, sizes, and the like).

An enlarged portion in FIG. 23 is a cross section of the lateral protrusion 55 formed at a corresponding portion so as to help understand of the description.

As shown in FIG. 23, the lateral protrusion 55 includes an upper edge 55*a* and a lower edge 55*b*, and the lower edge 55*b* undergoes a gentler rounding treatment than the upper edge 55*a*.

The "rounding" can be understood to mean a curved rounding in the embodiments of the present disclosure, and for convenience of manufacturing, it can be considered that a rounding range of the present embodiment includes even a case in which a straight line shaped portion (e.g., an edge) is included.

Since the lower edge 55*b* is rounded more gently than the upper edge 55*a*, the first sole 50 can be smoothly inserted into the second shoe sole 60 when the second shoe sole 60 is attached (inserted).

For example, as shown in FIG. 23, the upper edge 55*a* is formed to have an edge bent in a right angle or an angle close thereto, and when the wearer wearing the leg protector 1 according to the present embodiment is walking, the upper edge 55*a* inserted into the protrusion insertion recess 65 escapes upward from the protrusion insertion recess 65 to prevent detachment of the second shoe sole 60, thereby serving to maintain the coupling.

At this point, an upper side of the protrusion insertion recess 65 is preferably formed in a shape corresponding to a shape of an upper surface of the upper edge 55*a* so as to allow the upper edge 55*a* to be hooked.

For example, as shown in FIG. 22, the lateral wall 64 further includes a stepped part 66 formed at an inner side of the upper surface.

When the first sole 50 is inserted into and coupled to the second shoe sole 60, the stepped part 66 facilitates the insertion.

In other words, even in a state in which the first sole 50 is not exactly placed at the same position on the upper portion of the second shoe sole 60, when the first sole 50 and the second shoe sole 60 are placed at appropriate similar positions in a left-right direction of the foot of the wearer wearing the leg protector 1 according to the present embodiment and then the first sole 50 is pressed downward, even when the first sole 50 is partially hooked on the upper surface of the lateral wall 64, the first sole 50 may be inserted into and coupled to the second shoe sole 60 due to the stepped part 66.

Consequently, the stepped part 66 provides a clearance through which the first sole 50 is insertable into and couplable to the second shoe sole 60 and, simultaneously, provides a design element for preventing the upper surface of the inserted and coupled first sole 50 from being exposed to the outside.

For convenience of description, the leg protector 1 is omitted from FIGS. 21 and 23, and it can be understood that the leg protector 1 according to the present embodiment is coupled to the upper portion of the first sole 50 of FIG. 21.

Figure 25:
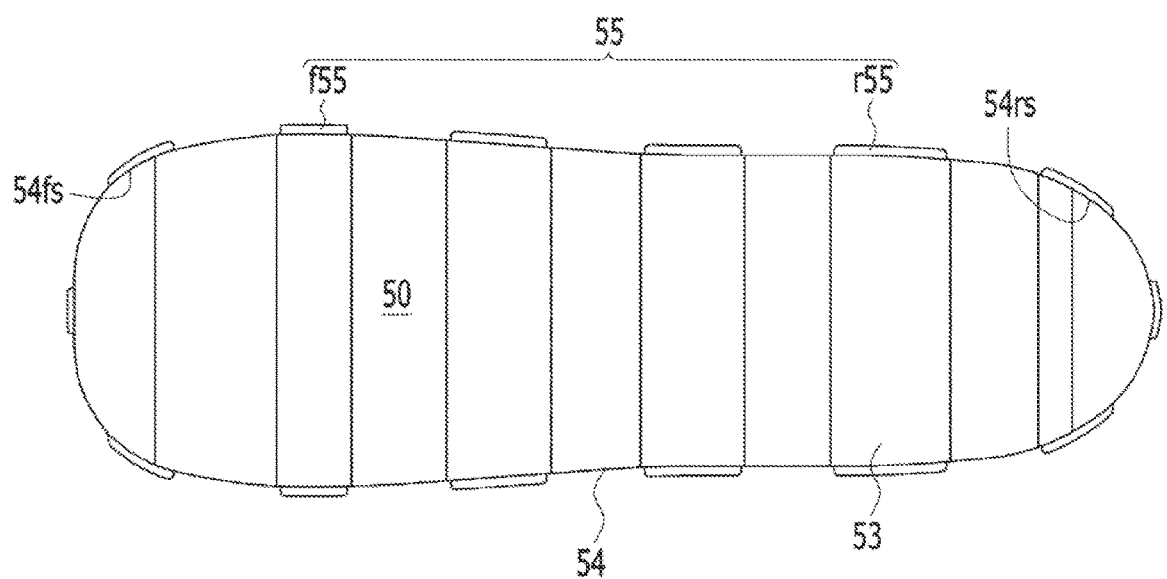
FIG. 25 is a bottom view of a first sole according to yet another embodiment of the present disclosure.
Figure 26:
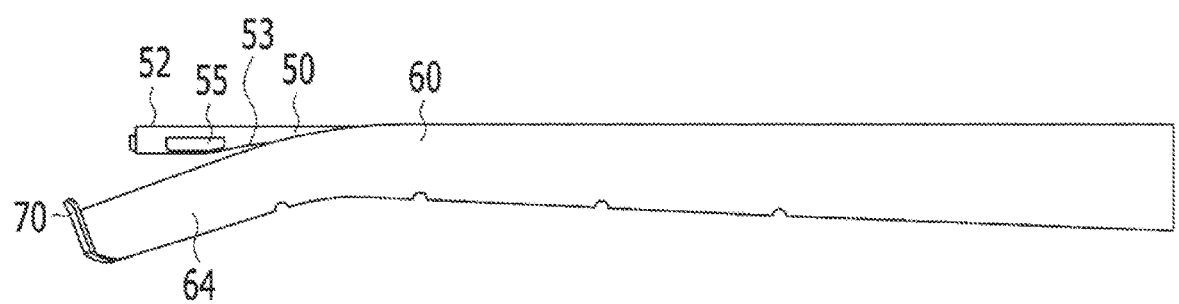
FIG. 26 is a diagram illustrating a state in which the sole portion of the leg protector according to yet another embodiment of the present disclosure is being detached.

FIG. 25 is a bottom view of a first sole according to yet another embodiment of the present disclosure. FIG. 26 is a diagram illustrating a state in which the sole portion of the leg protector according to yet another embodiment of the present disclosure is being detached.

One or more lateral protrusions 55 according to the present embodiment are formed on at least one portion among a lateral side of a lateral surface of the first sole plate part 52, a front side of a connection part 54*fs*, and a lateral side and a rear side of the connection part 54*rs*.

For example, as shown in FIG. 25, when the lateral protrusion 55 is formed at the lateral side of a lateral surface of the first sole plate part 52 and a front side of a connection part 54*fs*, and the second shoe sole 60 is detached from the leg protector 1 according to the present embodiment, continuity of detachment is provided due to the lateral protrusion 55 formed at the connection part 54*fs* such that detachment of the second shoe sole 60 is facilitated.

In the lateral protrusion 55 according to the present embodiment, an area of the lateral protrusion r55 provided at a front end is formed to be larger than that of the lateral protrusion f55 provided at a rear end.

As described above, the lateral protrusion 55 serves to perform and maintain the coupling so that it is preferable that an area of the lateral protrusion 55 at the rear end is formed to be larger than that thereof is larger at the front end, thereby facilitating the detachment. The area of the lateral protrusion 55 means an overall dimension of the lateral protrusion 55. For example, the area of the lateral protrusion 55 can be understood as an outer surface area or a cross-sectional area of the lateral protrusion 55.

For example, in the lateral surface 54 of the first sole plate part, an area in which the lateral surface 54 is formed is formed in the range of 10% to 50% of a total area of the lateral surface 54 of the first sole plate part.

In this case, the area of the lateral protrusion 55 can be understood as a cross-sectional area of a base portion.

Since a plurality of lateral protrusions 55 are formed at predetermined intervals instead of being formed to be long as one unity and are inserted into the protrusion insertion recesses 65, a portion at which each of the plurality of lateral protrusions 55 are formed is fixed. Consequently, even when an impact is applied to some of the plurality of lateral protrusions 55 and thus some of the plurality of lateral protrusions 55 is separated from the protrusion insertion recesses 65, the insert-fixed state of lateral protrusions 55, which are formed at other portions and inserted into the protrusion insertion recesses 65, is not affected.

When the area of the portion at which the lateral protrusion 55 is formed is greater than 50% or less than 10% of the total area of the lateral surface 54 of the first sole plate part, an effect of maintaining the coupling of the lateral protrusion 55 is reduced, and when an impact is applied to some of the second shoe sole 60 or the first sole 50, detachment of the second shoe sole 60 may be easily generated such that the area of the portion at which the lateral protrusion 55 is formed is preferably formed in the range of 10% to 50% of the total area of the lateral surface 54 of the first sole plate part.

For example, the leg protector 1 further includes a removal handle 70 provided at one side of the lateral wall 64.

The removal handle 70 is provided to allow the wearer to easily detach the second shoe sole 60 without holding a portion of the bottom surface of the second shoe sole 60. In order to prevent the second shoe sole 60 from being exposed to the outside and to allow the wearer to easily use the removal handle 70, the removal handle 70 is preferably formed to the upward side at a front surface of the lateral wall 64.

As shown in FIG. 26, the removal handle 70 is pulled downward such that the second shoe sole 60 is easily detached from the first sole 50.

A slip prevention part 67 for preventing slippage may be provided at the lower surface of the second sole plate part 62. For example, as shown in FIG. 24, the slip prevention part 67 may be formed in a recessed shape. Alternatively, the slip prevention part 67 may be formed in a protrusion shape.

The first sole 50 according to the present embodiment is formed of a material that is harder than that of the second shoe sole 60.

For example, the first sole 50 may be formed of a material that is harder than that of the second shoe sole 60. In this case, the first sole 50 may be made of EVA pylon, and the second shoe sole 60 may be made of a relatively soft EVA material.

Alternatively, it is also possible to control a degree of foaming without changing a material to cause a change in hardness.

Since the first sole 50 is formed of a material that is harder than that of the second shoe sole 60, the first sole 50 may be inserted while the second shoe sole 60 is appropriately opened when the first sole 50 is inserted into the second shoe sole 60, and even when the second shoe sole 60 is detached, the second shoe sole 60 is flexibly bent and separated such that the detachment may be easily performed.

Figure 27:
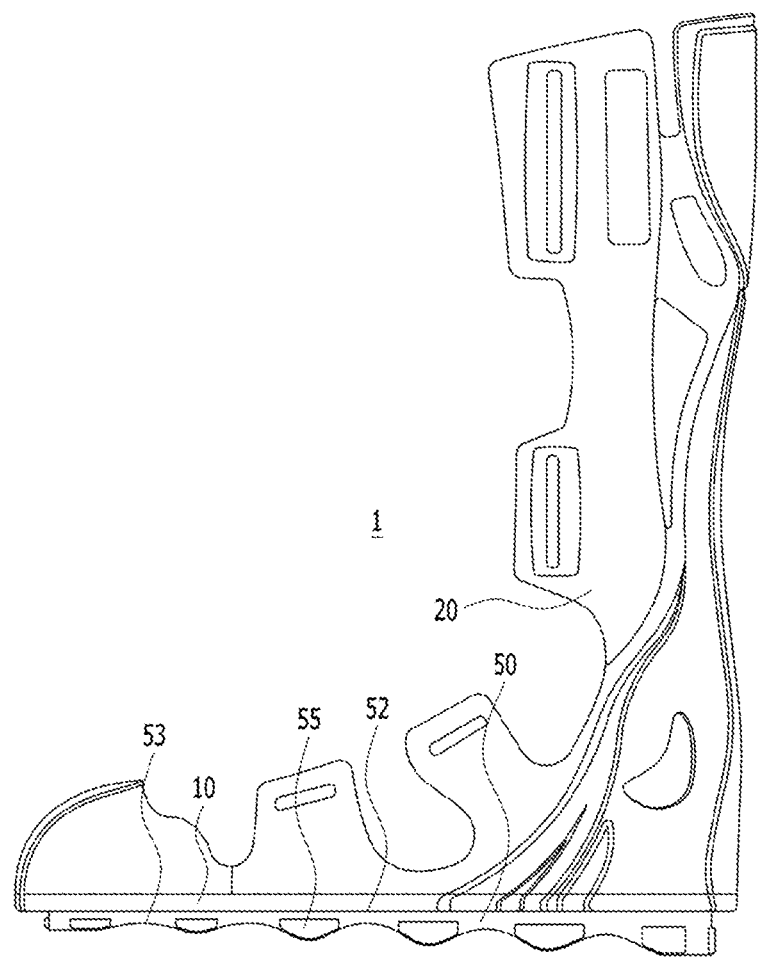
FIG. 27 is a side view illustrating a state in which the leg protector according to yet another embodiment of the present disclosure is used indoors.
Figure 28:
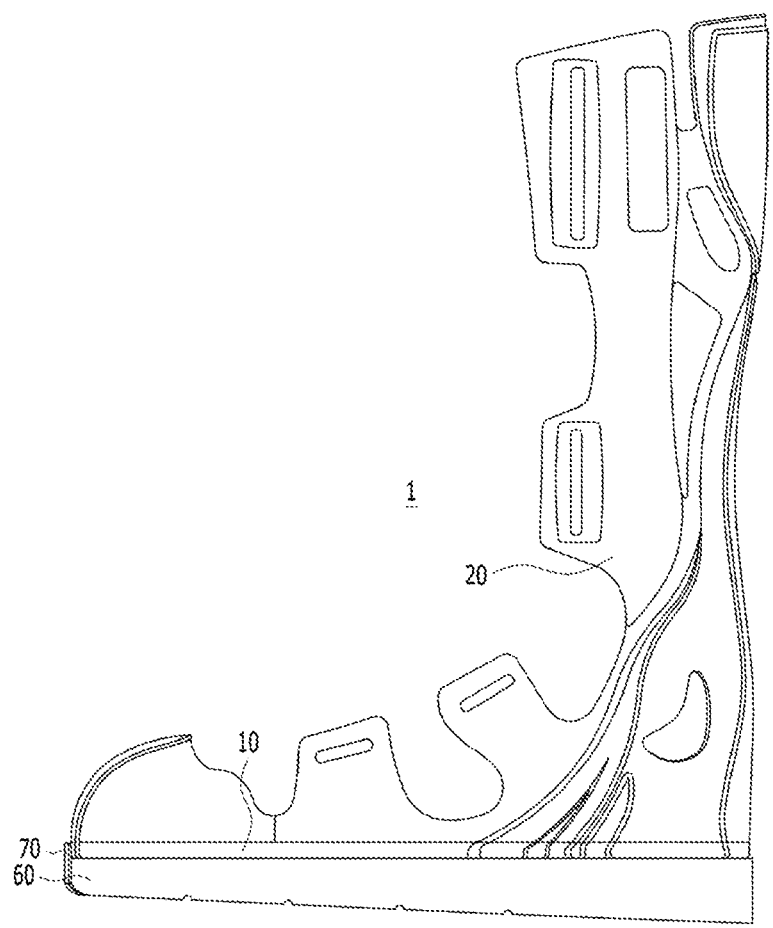
FIG. 28 is a side view illustrating a state in which the leg protector according to yet another embodiment of the present disclosure is used outdoors.

FIG. 27 is a side view illustrating a state in which the leg protector according to yet another embodiment of the present disclosure is used indoors. FIG. 28 is a side view illustrating a state in which the leg protector according to yet another embodiment of the present disclosure is used outdoors.

As shown in FIG. 28, when the second shoe sole 60 is coupled to the first sole 50 and a walking is performed outdoors, the first sole 50 and the second shoe sole 60 according to the present embodiment are formed such that the first sole 50 is not exposed to the outside.

Therefore, even when the walking is performed outdoors, contamination of the first sole 50 due to external dusts is minimized such that, as shown in FIG. 27, even though the walking is performed indoors with the first sole 50 in a state in which the second shoe sole 60 is detached, indoors are not contaminated.

The first sole 50 and the second shoe sole 60 of the leg protector 1 according to the present embodiment may be applied to various shoes having a structure and a shape different from those of the leg protector 1 according to the present embodiment.

In this case, the first sole 50 includes the first sole plate part 52 having the first bent part 53 which is provided at a lower surface of a bottom plate (not shown) of a shoe and at which a plurality of curves are disposed in a front-rear direction of the foot, and the plurality of lateral protrusions 55 formed along the lateral surface of the first sole plate part 52.

As described above, the first sole 50 may be provided at a lower side of the bottom plate (not shown) of the shoe in the form of an adhesive coupling, a fitting coupling, or the like.

Further, the second shoe sole 60 includes the second sole plate part 62 detachably coupled to the lower side of the first sole 50 and having a second bent part 63 formed in a curved shape corresponding to a shape of the first curved part 53 at an upper surface of the second sole plate part 62, the protrusion insertion recess 65 configured to allow each of the plurality of lateral protrusions 55 to be insertable into the protrusion insertion recess 65, and the lateral wall 64 formed along an edge of the second sole plate part 62.

Even when a shoe sole including the first sole 50 and the second shoe sole 60 is applied to a shoe not including the leg protector 1 according to the present embodiment, the shoe sole can provide an effect of allowing a free walking indoors and outdoors while maintaining a wearing state of the shoe.

While the present disclosure has been described to focus on exemplary embodiments thereof with reference to the accompanying drawings, various modifications can be devised by those skilled in the art without departing from the scope of the present disclosure. Accordingly, the scope of the present disclosure should be construed by the appended of the claims set forth as including such many modifications.

What is claimed is:

1. A leg protector made of an elastic material to protect a foot and a leg, the leg protector comprising:
 a bottom plate part configured to support the foot;
 a protection part formed to be connected to an upper side of the bottom plate part and to surround at least a portion of a rear surface portion and a lateral surface portion of the foot and the leg;
 a toe cover part provided at an upper side of a front surface portion of the bottom plate part and formed to surround toes from an upward side of the toes; and
 a detachable coupling part formed at a position of one side of the toe cover part and configured to allow the toe cover part to be detachable even in a state in which the leg protector is worn,
 wherein the toe cover part comprises a cover configured to protect the toes,
 the detachable coupling part comprises at least one elastic insertion piece formed at an end portion of the cover toward the bottom plate part and an insertion hole formed at a position of the bottom plate part corresponding to the at least one elastic insertion piece,
 the at least one elastic insertion piece is configured to be fitted and coupled to the insertion hole by an elastic force
 at least one protruding insertion piece is formed at a foremost end portion of the cover,
 a recess into which the at least one protruding insertion piece is insertable is formed at a position of the bottom plate part corresponding to each of the at least one protruding insertion piece,
 a cover engagement part formed at a lower end of the at least one protruding insertion piece and configured to be inserted into a lower side of the recess and hooked to a cover engagement bump formed at the lower side of the recess, and a gap is formed between the recess and the at least one protruding insertion piece located at the foremost end portion of the cover so as to allow the detachable coupling part to be released and the toe cover part to be pivoted and opened upward about the at least one protruding insertion piece located at the foremost end portion of the toe cover part.

2. The leg protector of claim 1, wherein:

the elastic insertion piece comprise a detachable part formed in a U-shape, and in a state of being coupled, one end of the detachable part is connected to the end portion of the cover and the other end of the detachable part is exposed to an upper side of the insertion hole, and a size of the U-shaped elastic insertion piece before contraction is formed to be greater than a size of the insertion hole.

3. The leg protector of claim 1, wherein:

the elastic insertion piece comprise a detachable part formed in a U-shape, and in a state of being coupled, one end of the detachable part is connected to the end portion of the cover and the other end of the detachable part is exposed to an upper side of the insertion hole, and a hook part is provided at one side of the other end of the elastic insertion piece and is hooked to a hook bump provided at one lateral surface of the insertion hole in a state of being coupled.

4. The leg protector of claim 1 wherein, in a state in which the detachable coupling part is released and the cover is pivoted and opened upward about the at least one protruding insertion piece located at the foremost end portion of the cover, the cover engagement part of the at least one protruding insertion piece is released from the cover engagement bump of the recess.

* * * * *